United States Patent
Muhsin et al.

(10) Patent No.: US 10,825,568 B2
(45) Date of Patent: Nov. 3, 2020

(54) ALARM NOTIFICATION SYSTEM

(71) Applicant: Masimo Corporation, Irvine, CA (US)

(72) Inventors: Bilal Muhsin, San Clemente, CA (US); Emil Sultanov, Anaheim, CA (US); Stephen Quong, Huntington Beach, CA (US)

(73) Assignee: Masimo Corporation, Irvine, CA (US)

( * ) Notice: Subject to any disclaimer, the term of this patent is extended or adjusted under 35 U.S.C. 154(b) by 60 days.

(21) Appl. No.: 15/927,887

(22) Filed: Mar. 21, 2018

(65) Prior Publication Data

US 2018/0218792 A1 Aug. 2, 2018

Related U.S. Application Data

(62) Division of application No. 14/511,972, filed on Oct. 10, 2014.

(Continued)

(51) Int. Cl.
*G16H 50/30* (2018.01)
*G06F 19/00* (2018.01)
(Continued)

(52) U.S. Cl.
CPC .............. *G16H 50/30* (2018.01); *G06F 19/00* (2013.01); *G06F 19/3418* (2013.01); *G16H 10/60* (2018.01); *G16H 40/20* (2018.01)

(58) Field of Classification Search
CPC .............. G06F 19/325; G06F 19/3481; G06F 19/3418; G06F 19/324; G06F 19/34;
(Continued)

(56) References Cited

U.S. PATENT DOCUMENTS

| 3,646,606 | A | 2/1972 | Buxton et al. |
| 3,690,313 | A | 9/1972 | Weppner et al. |

(Continued)

FOREIGN PATENT DOCUMENTS

| CN | 202889636 | 4/2013 |
| EP | 0 735 499 | 10/1996 |

(Continued)

OTHER PUBLICATIONS

US 8,845,543 B2, 09/2014, Diab et al. (withdrawn)

(Continued)

*Primary Examiner* — Joseph D Burgess
(74) *Attorney, Agent, or Firm* — Knobbe Martens Olson & Bear LLP

(57) ABSTRACT

An alarm notification system can enable a clinician to respond to an alarm notification received via a computing device, which may have more advanced functionality than a pager. The clinician's device can include a notification client which can respond to alarm notifications. The notification client can also provide one or more user interfaces that enable the clinician to view information about an alarm, such as information about a patient's status, physiological parameter values, trend data, audio/video of the patient, combinations of the same, or the like. Further, the notification client can provide functionality for a clinician to respond to an alarm, annotate an alarm, and/or indicate that the clinician can or cannot respond to the alarm, among other features. In addition, the clinician device can also (or instead) include an admit module that provides for automatic association of a patient to a device or location.

13 Claims, 28 Drawing Sheets

Related U.S. Application Data

(60) Provisional application No. 61/890,076, filed on Oct. 11, 2013.

(51) Int. Cl.
*G16H 10/60* (2018.01)
*G16H 40/20* (2018.01)

(58) Field of Classification Search
CPC ........ G06Q 50/22; G06Q 50/24; G16H 10/60;
G16H 40/20; G16H 50/20; G16H 40/63;
G16H 15/00; G16H 20/13; G16H 40/00;
G16H 50/30; G16H 80/00; G16H 10/20;
G16H 40/40; G16H 50/70; G16H 10/40;
G16H 10/65; G16H 20/10; G16H 20/17;
G16H 20/40; G16H 40/67; G16H 50/50;
G16H 70/00
See application file for complete search history.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,827,943 A | 5/1989 | Bornn et al. |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A * | 6/1994 | Russek ............... A61B 5/0002 340/573.1 |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Shimizu |
| 5,375,604 A | 12/1994 | Kelly et al. |
| 5,377,676 A | 1/1995 | Vari et al. |
| 5,400,794 A | 3/1995 | Gorman |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,462,051 A | 10/1995 | Oka et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang et al. |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,754,111 A | 5/1998 | Garcia |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,876,351 A | 3/1999 | Rohde |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,942,986 A | 8/1999 | Shabot et al. |
| 5,951,469 A | 9/1999 | Yamaura |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |

(56) References Cited

U.S. PATENT DOCUMENTS

| | | |
|---|---|---|
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang et al. |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,332,100 B1 | 12/2001 | Sahai et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,406,426 B1 | 6/2002 | Reuss et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,480,505 B1 | 11/2002 | Johansson et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 | 2/2003 | David et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,570,592 B1 | 5/2003 | Sajdak et al. |
| 6,578,428 B1 | 6/2003 | Dromms et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kiani et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |

(56) References Cited

U.S. PATENT DOCUMENTS

| | | |
|---|---|---|
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,730,026 B2 | 5/2004 | Christ et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,893,396 B2 | 5/2005 | Schulze et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,952,340 B2 | 10/2005 | Son |
| 6,956,649 B2 | 10/2005 | Acosta et al. |
| 6,957,107 B2 | 10/2005 | Rogers et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,042,338 B1 | 5/2006 | Weber |
| 7,044,918 B2 | 5/2006 | Diab |
| 7,044,930 B2 | 5/2006 | Stromberg |
| 7,048,687 B1 | 5/2006 | Reuss et al. |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,691 B1 | 8/2007 | Asomani |
| 7,261,697 B2 | 8/2007 | Berstein |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,141 B2 | 11/2007 | Staats et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,327,219 B2 | 2/2008 | Lederer |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |

(56) References Cited

U.S. PATENT DOCUMENTS

| | | |
|---|---|---|
| 7,390,299 B2 | 6/2008 | Weiner et al. |
| 7,395,158 B2 | 7/2008 | Monfre et al. |
| 7,395,216 B2 | 7/2008 | Rosenfeld |
| 7,402,338 B2 | 7/2008 | Weintritt et al. |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,523,044 B2 | 4/2009 | Rosenblood |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,671,733 B2 | 3/2010 | McNeal et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,749,164 B2 | 7/2010 | Davis |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,844 B2 | 5/2011 | Moberg et al. |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,978,062 B2 | 7/2011 | LaLonde et al. |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Ali et al. |
| 7,991,463 B2 | 8/2011 | Kelleher et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |

(56) References Cited

U.S. PATENT DOCUMENTS

| | | |
|---|---|---|
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,298,153 B2 | 10/2012 | Boute et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,326,649 B2 | 12/2012 | Rosenfeld |
| 8,327,002 B1 | 12/2012 | Van Dussen |
| 8,328,793 B2 | 12/2012 | Birkenbach et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,167 B2 | 7/2013 | Buxton et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,578,082 B2 | 11/2013 | Medina et al. |
| 8,579,813 B2 | 11/2013 | Causey, III et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,612,260 B2 | 12/2013 | Hasan et al. |
| 8,620,678 B2 | 12/2013 | Gotlib |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,655,680 B2 | 2/2014 | Bechtel et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,694,331 B2 | 4/2014 | DeBelser et al. |

(56) References Cited

U.S. PATENT DOCUMENTS

| | | |
|---|---|---|
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,717,909 B1 | 5/2014 | Shekhar et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,020 B2 | 6/2014 | Burdea et al. |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,054 B2 | 9/2014 | Weiss |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,956,294 B2 | 2/2015 | McCombie et al. |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 8,998,830 B2 | 4/2015 | Halperin et al. |
| 9,028,429 B2 | 5/2015 | Telfort et al. |
| 9,037,207 B2 | 5/2015 | Al-Ali et al. |
| 9,041,530 B2 | 5/2015 | Sprigg et al. |
| 9,057,689 B2 | 6/2015 | Soller |
| 9,058,635 B1 | 6/2015 | Rybkin |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,578 B2 | 9/2015 | Grunwald |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,384,652 B2 | 7/2016 | Gilham et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |

(56) References Cited

U.S. PATENT DOCUMENTS

| | | |
|---|---|---|
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Al-Ali et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |

(56) References Cited

U.S. PATENT DOCUMENTS

| | | |
|---|---|---|
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,512,436 B2 | 12/2019 | Muhsin et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,667,764 B2 | 6/2020 | Ahmed et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039483 A1 | 11/2001 | Brand et al. |
| 2001/0046366 A1 | 11/2001 | Susskind |
| 2001/0051765 A1 | 12/2001 | Walker et al. |
| 2002/0010401 A1 | 1/2002 | Bushmakin et al. |
| 2002/0038392 A1* | 3/2002 | De La Huerga .. A61M 5/14212 710/8 |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0099275 A1 | 7/2002 | Schmidt et al. |
| 2002/0133080 A1 | 9/2002 | Apruzzese et al. |
| 2002/0140675 A1 | 10/2002 | Ali et al. |
| 2002/0177758 A1 | 11/2002 | Schoenberg |
| 2002/0198445 A1 | 12/2002 | Dominguez et al. |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0149598 A1 | 8/2003 | Santoso et al. |
| 2003/0156288 A1 | 8/2003 | Barnum et al. |
| 2003/0158466 A1 | 8/2003 | Lynn et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0059599 A1 | 3/2004 | McIvor |
| 2004/0106163 A1 | 6/2004 | Workman, Jr. et al. |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0172222 A1* | 9/2004 | Simpson ............... G08B 21/02 702/189 |
| 2004/0172302 A1 | 9/2004 | Martucci et al. |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055242 A1 | 3/2005 | Bello et al. |
| 2005/0055276 A1 | 3/2005 | Kiani et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0143671 A1 | 6/2005 | Hastings et al. |
| 2005/0146431 A1 | 7/2005 | Hastings et al. |
| 2005/0148890 A1 | 7/2005 | Hastings |
| 2005/0164933 A1 | 7/2005 | Tymianski et al. |
| 2005/0190747 A1 | 9/2005 | Sindhwani et al. |
| 2005/0191294 A1 | 9/2005 | Arap et al. |
| 2005/0203775 A1 | 9/2005 | Achan |
| 2005/0234317 A1 | 10/2005 | Kiani |
| 2005/0268401 A1 | 12/2005 | Dixon et al. |
| 2005/0277872 A1 | 12/2005 | Colby, Jr. et al. |
| 2006/0049936 A1* | 3/2006 | Collins, Jr. ............ A61B 5/1115 340/539.11 |
| 2006/0058647 A1 | 3/2006 | Strommer et al. |
| 2006/0073719 A1 | 4/2006 | Kiani |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0169773 A1 | 8/2006 | Lyons et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0073555 A1 | 3/2007 | Buist |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0157285 A1 | 7/2007 | Frank et al. |

(56) References Cited

U.S. PATENT DOCUMENTS

| | | |
|---|---|---|
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0192140 A1 | 8/2007 | Gropper |
| 2007/0213600 A1 | 9/2007 | John et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg et al. |
| 2007/0282478 A1 | 12/2007 | Al-Ali et al. |
| 2008/0000479 A1 | 1/2008 | Elaz et al. |
| 2008/0001735 A1 | 1/2008 | Tran |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0039701 A1 | 2/2008 | Ali et al. |
| 2008/0053438 A1 | 3/2008 | DeVries et al. |
| 2008/0058657 A1 | 3/2008 | Schwartz et al. |
| 2008/0064965 A1 | 3/2008 | Jay et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0201174 A1 | 8/2008 | Ramasubramanian et al. |
| 2008/0208912 A1 | 8/2008 | Garibaldi |
| 2008/0221396 A1 | 9/2008 | Garces et al. |
| 2008/0221418 A1 | 9/2008 | Al-Ali et al. |
| 2008/0228077 A1 | 9/2008 | Wilk et al. |
| 2008/0249804 A1 | 10/2008 | Kim |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0046837 A1 | 2/2009 | Thiel |
| 2009/0052623 A1 | 2/2009 | Tome et al. |
| 2009/0054735 A1 | 2/2009 | Higgins et al. |
| 2009/0054743 A1 | 2/2009 | Wekell et al. |
| 2009/0062682 A1 | 3/2009 | Bland et al. |
| 2009/0069642 A1 | 3/2009 | Gao et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0119330 A1 | 5/2009 | Sampath et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0204977 A1 | 8/2009 | Tavares et al. |
| 2009/0221880 A1 | 9/2009 | Soderberg et al. |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson et al. |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0088121 A1 | 4/2010 | Shih et al. |
| 2010/0099964 A1 | 4/2010 | O'Reilly et al. |
| 2010/0125217 A1 | 5/2010 | Kuo et al. |
| 2010/0144627 A1 | 6/2010 | Vitek et al. |
| 2010/0185101 A1 | 7/2010 | Sakai et al. |
| 2010/0188230 A1 | 7/2010 | Lindsay |
| 2010/0198622 A1 | 8/2010 | Gajic et al. |
| 2010/0210958 A1 | 8/2010 | Manwaring et al. |
| 2010/0234718 A1 | 9/2010 | Sampath et al. |
| 2010/0270257 A1 | 10/2010 | Wachman et al. |
| 2010/0298650 A1 | 11/2010 | Moon et al. |
| 2010/0298659 A1 | 11/2010 | McCombie et al. |
| 2010/0298661 A1 | 11/2010 | McCombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0106561 A1* | 5/2011 | Eaton, Jr. ............ G06Q 10/087 705/3 |
| 2011/0106565 A1 | 5/2011 | Compton et al. |
| 2011/0118561 A1 | 5/2011 | Tari et al. |
| 2011/0118573 A1 | 5/2011 | Mckenna |
| 2011/0125060 A1 | 5/2011 | Telfort et al. |
| 2011/0130636 A1 | 6/2011 | Daniel |
| 2011/0137297 A1 | 6/2011 | Kiani et al. |
| 2011/0152629 A1 | 6/2011 | Eaton et al. |
| 2011/0166465 A1 | 7/2011 | Clements et al. |
| 2011/0167133 A1 | 7/2011 | Jain |
| 2011/0172498 A1 | 7/2011 | Olsen et al. |
| 2011/0172967 A1 | 7/2011 | Al-Ali et al. |
| 2011/0178373 A1 | 7/2011 | Pacey et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213210 A1 | 9/2011 | Temby et al. |
| 2011/0213212 A1 | 9/2011 | Al-Ali |
| 2011/0227739 A1 | 9/2011 | Gilham et al. |
| 2011/0230733 A1 | 9/2011 | Al-Ali |

(56) References Cited

U.S. PATENT DOCUMENTS

| | | |
|---|---|---|
| 2011/0237911 A1 | 9/2011 | Lamego et al. |
| 2011/0237969 A1 | 9/2011 | Eckerbom et al. |
| 2011/0257544 A1 | 10/2011 | Kaasinen et al. |
| 2011/0263950 A1 | 10/2011 | Larson et al. |
| 2011/0288383 A1 | 11/2011 | Diab |
| 2011/0295094 A1 | 12/2011 | Doyle et al. |
| 2011/0301444 A1 | 12/2011 | Al-Ali |
| 2012/0002791 A1 | 1/2012 | Kraus et al. |
| 2012/0004579 A1 | 1/2012 | Luo et al. |
| 2012/0025992 A1 | 2/2012 | Tallent et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0041316 A1 | 2/2012 | Al-Ali et al. |
| 2012/0046557 A1 | 2/2012 | Kiani |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0075464 A1 | 3/2012 | Derenne et al. |
| 2012/0088984 A1 | 4/2012 | Al-Ali et al. |
| 2012/0095778 A1 | 4/2012 | Gross et al. |
| 2012/0101353 A1 | 4/2012 | Reggiardo et al. |
| 2012/0112903 A1 | 5/2012 | Kaib et al. |
| 2012/0116175 A1 | 5/2012 | Al-Ali et al. |
| 2012/0123231 A1 | 5/2012 | O'Reilly |
| 2012/0123799 A1 | 5/2012 | Nolen et al. |
| 2012/0134257 A1 | 5/2012 | Knox |
| 2012/0136221 A1 | 5/2012 | Killen et al. |
| 2012/0165629 A1 | 6/2012 | Merritt et al. |
| 2012/0179006 A1 | 7/2012 | Jansen et al. |
| 2012/0184120 A1 | 7/2012 | Basta et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran et al. |
| 2012/0265039 A1 | 10/2012 | Kiani |
| 2012/0278104 A1* | 11/2012 | Traughber ......... G08B 21/0277 705/3 |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0293323 A1 | 11/2012 | Kaib et al. |
| 2012/0294801 A1 | 11/2012 | Scherz et al. |
| 2012/0296178 A1 | 11/2012 | Lamego et al. |
| 2012/0302894 A1 | 11/2012 | Diab et al. |
| 2012/0303476 A1 | 11/2012 | Krzyzanowski et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0012830 A1 | 1/2013 | Leininger |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0046197 A1 | 2/2013 | Dlugos, Jr. et al. |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0069802 A1 | 3/2013 | Foghel et al. |
| 2013/0079610 A1 | 3/2013 | Al-Ali |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0123616 A1 | 5/2013 | Merritt et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0197364 A1 | 8/2013 | Han |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens et al. |
| 2013/0345921 A1 | 12/2013 | Al-Ali et al. |
| 2014/0012100 A1 | 1/2014 | Al-Ali et al. |
| 2014/0022081 A1 | 1/2014 | Ribble et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0081090 A1 | 3/2014 | Picard et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0097961 A1* | 4/2014 | Vaglio ................. G06F 19/3418 340/691.6 |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0152673 A1 | 6/2014 | Lynn et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0257057 A1 | 9/2014 | Reis Cunha et al. |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |

(56) References Cited

U.S. PATENT DOCUMENTS

| | | |
|---|---|---|
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0343889 A1 | 11/2014 | Ben Shalom et al. |
| 2014/0357966 A1 | 12/2014 | Al-Ali et al. |
| 2014/0358574 A1 | 12/2014 | Tara et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0001302 A1 | 1/2015 | Gelay et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0220696 A1 | 8/2015 | Lekutai et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0321904 A1 | 11/2016 | Johnson et al. |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0235910 A1 | 8/2017 | Cantillon et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |

(56) References Cited

U.S. PATENT DOCUMENTS

| | | |
|---|---|---|
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060629 A1 | 2/2020 | Muhsin et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |

FOREIGN PATENT DOCUMENTS

| | | |
|---|---|---|
| EP | 1 075 831 | 2/2001 |
| EP | 1 226 783 | 7/2002 |
| EP | 2 335 569 | 6/2011 |
| EP | 2 766 834 | 8/2014 |
| EP | 2 811 894 | 12/2014 |
| JP | 10-336064 | 12/1998 |
| JP | 2002-513602 | 5/2002 |
| JP | 2002-165764 | 6/2002 |
| JP | 2002-172096 | 6/2002 |
| JP | 2002-542493 | 12/2002 |
| JP | 2005-218036 | 8/2005 |
| JP | 2005-295375 | 10/2005 |
| JP | 2007-021213 | 2/2007 |

(56) References Cited

FOREIGN PATENT DOCUMENTS

| | | |
|---|---|---|
| JP | 2007-095365 | 4/2007 |
| JP | 2007-174051 | 7/2007 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-524510 | 7/2010 |
| JP | 2011-519607 | 7/2011 |
| JP | 2011-519684 | 7/2011 |
| JP | 2011-152261 | 8/2011 |
| JP | 2014-533997 | 12/2014 |
| WO | WO 98/029790 | 7/1998 |
| WO | WO 99/013766 | 3/1999 |
| WO | WO 99/056613 | 11/1999 |
| WO | WO 00/063713 | 10/2000 |
| WO | WO 2004/056266 | 7/2004 |
| WO | WO 2004/059551 | 7/2004 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2013/056160 | 4/2013 |
| WO | WO 2013/119982 | 8/2013 |
| WO | WO 2015/054665 | 4/2015 |
| WO | WO 2019/204368 | 10/2019 |

OTHER PUBLICATIONS

Cahalin et al., "The Six-Minute Walk Test Predicts Peak Oxygen Uptake and Survival in Patients with Advanced Heart Failure", Chest, 110(2):325-332, (Aug. 1996), Downloaded from http://journal.publications.chestnet.org/ on Oct. 16, 2013.

Capuano et al., "Remote Telemetry—New Twists for Old Technology", Nursing Management, Jul. 1995, vol. 26, No. 7, pp. 26-32.

Elmer-Dewitt, Philip, "Apple's iWatch: The killer apps may be in hospitals, not health clubs", Fortune.com, Feb. 3, 2014, http://fortune.com/2014/02/03/apples-iwatch-the-killer-apps-may-be-in-hospitals-not-health-clubs/, 4 pages.

Grundy et al., "Telemedicine in Critical Care: An Experiment in Health Care Delivery", JACEP, Oct. 1977, vol. 6, No. 10, pp. 439-444.

Grundy et al., "Telemedicine in Critical Care: Problems in Design, Implementation and Assessment", Jul. 1982, vol. 10, No. 7, pp. 471-475.

"Multihoming"—Wikipedia, the free encyclopedia, Retrieved from http://en.wikipedia.org/w/index.php?title=Multihoming&oldid=511630157 on Sep. 25, 2012.

Ruppen et al., "A WoT Approach to eHealth: Case Study of a Hospital Laboratory Alert Escalation System", Proceedings of the Third International Workshop on the Web of Things; 2012, vol. 1. No. 6, pp. 6.

Rysavy, Peter, "Making the Call with Two-Way Paging", Network Computing, Published Jan. 15, 1997, www.rysavy.com/Articles/twoway.htm, pp. 5.

Wachter et al., "The Employment of an Iterative Design Process to Develop a Pulmonary Graphical Display", Journal of the American Medical Informatics Association, vol. 10, No. 4, Jul./Aug. 2003, pp. 363-372.

U.S. Appl. No. 15/498,194, Intelligent Medical Escalation Process, filed Apr. 26, 2017.

U.S. Appl. No. 14/511,972, Alarm Notification System, filed Oct. 10, 2014.

U.S. Appl. No. 16/388,637, Mobile Patient Alarm Display, filed Apr. 18, 2019.

International Search Report & Written Opinion in PCT Application No. PCT/US2019/027772, dated Aug. 29, 2019.

Invitation to Pay Additional Fees in PCT Application No. PCT/US2019/027772, dated Jul. 5, 2019.

\* cited by examiner admit patient

| | | |
|---|---|---|
| last name | | 🔍 ← 2210 |
| first name | | ← 2220 |
| middle name | | |
| primary assignment | -- | 🔍 ← 2230 |
| secondary assignment | -- | 🔍 |

| | |
|---|---|
| label | |
| room | | ← 2240
| notes | |

Admit

FIG. 22 admit patient

| | |
|---|---|
| last name | Galt |
| first name | John |
| middle name | R |
| primary assignment | -- |
| secondary assignment | -- |

| | |
|---|---|
| label | jgalt |
| room | 101 |
| notes | |

Admit ◄— 2510

FIG. 25 vital signs verification

| | |
|---:|:---:|
| % SpO$_2$ | 97 |
| % SpfO$_2$ | 95 |
| PR bpm | 74 |
| RRa rpm | 15 |
| SpHb g/dl | 13.4 |
| PVI | 20 |
| SpMet | 1.0 |
| SpCO | 1 |
| PI | 4.0 |
| SpOC | 18 |
| Temperature °F | ✏ |
| NIBP | ✏ |
| level of consciousness | -- |
| pain scale | -- |

Cancel    Approve

Galt, John RM 101

FIG. 27

ALARM NOTIFICATION SYSTEM

INCORPORATION BY REFERENCE TO ANY RELATED APPLICATIONS

Any and all applications, if any, for which a foreign or domestic priority claim is identified in the Application Data Sheet of the present application are hereby incorporated by reference under 37 CFR 1.57.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, $SpO_2$ level, pulse, and blood pressure, among others. Clinicians, including doctors, nurses, physician's assistants, and other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as $SpO_2$ and pulse rate in addition to advanced parameters, such as HbCO, HbMet and total hemoglobin (Hbt, THb, or SpHb) and corresponding multiple wavelength optical sensors are described in at least U.S. patent application Ser. No. 11/367,013, filed Mar. 1, 2006 and entitled Multiple Wavelength Sensor Emitters and U.S. patent application No. Ser. No. 11/366,208, filed Mar. 1, 2006 and entitled Noninvasive Multi-Parameter Patient Monitor, both assigned to Masimo Laboratories, Irvine, Calif. (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index, signal quality, HbCO, and HbMet among other parameters are also available from Masimo Corporation, Irvine, Calif. (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt or SpHb), as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, which are each hereby incorporated by reference herein in their entirety. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index (PI), signal quality (SiQ), pulse variability index (PVI), HbCO and HbMet among other parameters are also available from Masimo.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

An alarm notification system can enable a clinician to respond to an alarm notification received via a computing device, which may have more advanced functionality than a pager. The clinician's device can include a notification client which can respond to alarm notifications. The notification client can also provide one or more user interfaces that enable the clinician to view information about an alarm, such as information about a patient's status, physiological parameter values, trend data, audio/video of the patient, combinations of the same, or the like. Further, the notification client can provide functionality for a clinician to respond to an alarm, annotate an alarm, and/or indicate that the clinician can or cannot respond to the alarm, among other features. In addition, the clinician device can also (or instead) include an admit module that provides for automatic association of a patient to a device or location.

Once a patient has been admitted (or optionally after), vital signs can be captured by the patient device and/or by the clinician and submitted via the patient device for inclusion in the patient's electronic medical record.

BRIEF DESCRIPTION OF THE DRAWINGS

Throughout the drawings, reference numbers are re-used to indicate correspondence between referenced elements. The drawings are provided to illustrate embodiments of the inventions described herein and not to limit the scope thereof.

FIGS. 22 through 25 depict example monitoring device user interfaces for admitting a patient to the device.

FIG. 27 depicts an example monitoring device user interface that includes functionality for submitting vital signs.

DETAILED DESCRIPTION

I. Introduction

Figure 1:
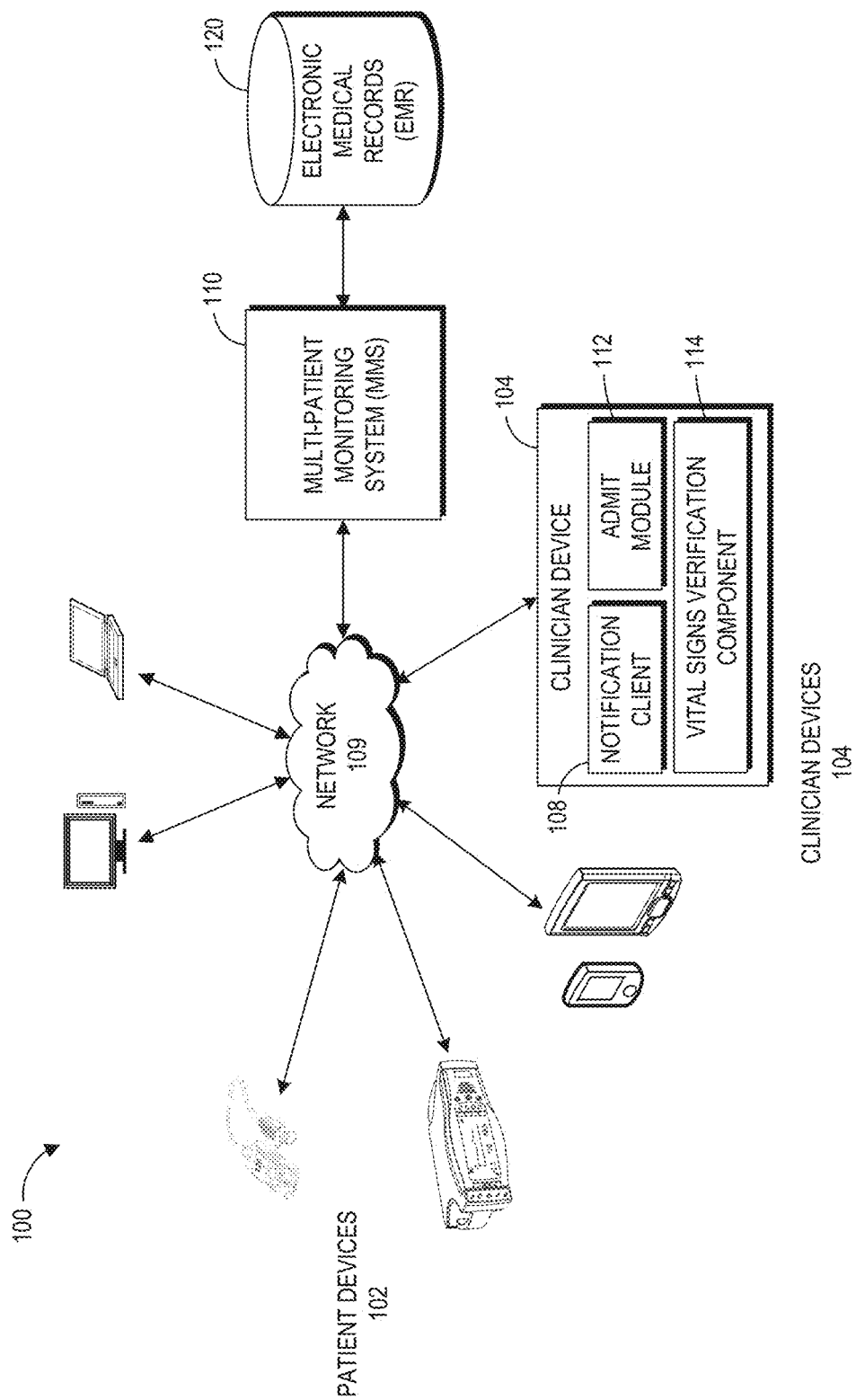
FIG. 1 depicts an embodiment of a clinical computing environment that includes a multi-patient monitoring system.

Patient monitors typically monitor patients' physiological parameters to determine whether the parameters are within safe limits. If a physiological parameter exceeds a safety limit or threshold, or is otherwise trending toward a dangerous condition, a patient monitor can generate an alarm. The alarm may have audible and/or visual characteristics. Typically, the patient monitor sounds an alarm to attract the attention of nearby clinicians to alert the clinicians that the patient may need medical attention. Clinicians within earshot can respond to the patient and clear the alarm. In addition, some patient monitors send alarms over a network to a computer system at a nurse's station to alert the clinicians at the nurse's station. Still other patient monitors send alarms over a network to a paging system, which in turn pages clinicians regarding the alarm. As a result, clinicians who are not within earshot of the audible alarm can still be alerted to the alarm condition and provide a response.

A typical pager system includes a paging appliance or server that receives a notification from a patient device of an alarm condition and forwards a simple alarm message to one or more clinicians' pagers. The alarm message may include information about the patient's name or room number and possibly limited information about the alarm itself (such as "low $SpO_2$"). Pagers used in hospitals and other clinical facilities are typical one way, unidirectional devices and therefore do not provide functionality for clinicians to respond to a page using the pager device itself. Accordingly, a pager system cannot tell if a clinician is going to respond to the alarm. The pager system may instead monitor whether the alarm has been cleared, and after the alarm has not been cleared for a certain amount of time, escalate the alarm to a second clinician (or group of clinicians). During the time when the pager system is waiting to see if the alarm has been cleared, patients may worsen and suffer adverse health effects. Accordingly, pager systems are limited in their capacity to improve patient care outcomes.

This disclosure describes embodiments of alarm notification systems that can enable a clinician to respond to an alarm notification received via a computing device, which may have more advanced functionality than a pager. The clinician device may be, for instance, a cellphone or smartphone, tablet, laptop, personal digital assistant (PDA), or the like. In certain embodiments, the clinician's device includes a notification client which may be a mobile software application, web application, or the like that can respond to alarm notifications. The notification client can also provide one or more user interfaces that enable the clinician to view information about an alarm, such as information about a patient's status, physiological parameter values, trend data, video of the patient, combinations of the same, or the like. Further, the notification client can provide functionality for a clinician to respond to an alarm, annotate an alarm, and/or indicate that the clinician can or cannot respond to the alarm, among other features. Advantageously, in certain embodiments, the notification client can enable a clinician to respond and indicate his or her availability or unavailability to handle the alarm, thereby facilitating more intelligent and rapid escalation to improve patient outcomes.

The clinician device may also include other functionality that improves other aspects of patient care. For instance, the clinician device may assist with keeping track of which patient monitoring devices are associated with which patients. Currently, clinicians type patient names into a computer system to associate patients with patient devices. Human error from mistyping may result in patients being associated with the wrong devices. Consequently, an alarm from a device may trigger a response that goes to the wrong room. As a result, a patient may not be reached in time to address the cause of the alarm or may otherwise suffer a poorer outcome.

Thus, in certain embodiments, the clinician device also includes an admit module that provides for automatic association of a patient to a device. The admit module may include a scanner application or the like that can scan a patient tag and a device tag, obtain identifiers from each tag, and couple the tags in physical computer storage (such as in an electronic medical records system). The tags may be machine-readable codes in the form of one-dimensional or two-dimensional barcodes such as UPC barcodes, quick response (QR) codes, Data Matrix codes, Aztec codes, Microsoft Tag barcodes or High Capacity Color Barcodes, Shotcode, Semacode, SPARQcode, PDF417 barcodes, Cauzin Softstrip codes, and the like, as well as radio-frequency identifiers (RFID), combinations of the same, or the like. Further, the admit component may also include functionality for associating the patient with a location such as a room, bed, bassinet (for infants), or the like.

Further, the patient monitor can include a vital signs verification component that includes functionality for initiating a vital signs submission process for an admitted patient. Once a patient has been admitted (or optionally thereafter), vital signs can be captured by the patient device and/or by the clinician and submitted via the patient device to a server system for inclusion in the patient's electronic medical record.

II. Example Clinical Computing Environment

Turning to FIG. 1, an embodiment of a clinical computing environment 100 is shown. The clinical computing environment 100 may be implemented in one or more hospitals or other clinical facilities. Further, the clinical computing environment 100 can facilitate monitoring patients within their homes if such patients are using network-enabled monitoring equipment.

In the clinical computing environment 100, various patient devices 102, clinician devices 104, and nurse's station systems or kiosks 106 communicate over a network 109 with a multi-patient monitoring system (MMS) 110. The network 109 may include a local area network (LAN), a wide area network (WAN), a public network (such as the Internet), a private network, or any combination of the same. For instance, the network 109 can include a wireless and/or wired hospital network or a network that connects multiple clinical facilities.

The patient devices 102 may be any of the patient monitors or monitoring devices described herein and may include bedside monitors, ambulatory or mobile monitors, in-home monitors, and the like. The patient devices 102 can receive input from physiological sensors coupled with a patient and may measure parameters such as oxygen saturation or $SpO_2$, respiratory rate, blood pressure, heart rate or pulse rate perfusion, other blood gas parameters, brain activity, brain oxygen saturation, any of the other parameters described herein, and the like. The patient devices 102 can provide information about a patient's status, including current values of physiological parameters, trend values, and historical values of physiological parameters over the network 109 to the MMS 110. The MMS 110 can in turn store this data in an electronic medical records (EMR) system 120.

In addition, the MMS 110 can provide this data to the nurse's station systems 106. The nurse's station systems 106 can include any type of computing device including, but not limited to, a desktop, laptop, tablet, phone or the like. The nurse's station systems 106 may also include clinical facility kiosks such as computers on wheels (COWs), which may be dispersed throughout a clinical facility. The nurse's station systems 106 can communicate with a plurality of patient devices 102 to receive information of a plurality of patients so that the nurse's station systems 106 can provide clinicians with the ability to monitor physiological parameter data for a plurality of patients.

In addition, in some embodiments (not shown) patients' rooms may be equipped with video monitoring equipment that can provide video views of patients so as to view patients remotely (e.g., for telemedicine purposes). Such video data may be provided over the network 109 to the nurse's station systems 106, to the MMS 110, and/or to clinician devices 104 (see, e.g., FIG. 17). The video data may be captured by video cameras installed in the patient devices 102 or with separate video camera installed in patient rooms or the like.

The clinician devices 104 can include any device including a laptop, tablet, cell phone, smartphone, personal digital assistant (PDA), or any other device (including desktop systems). In the depicted embodiment, the clinician devices 104 include a notification client 108 that can receive alarm notifications from the patient devices 102 through the MMS 110. In an embodiment, when a patient device 102 detects that a parameter of a patient has exceeded a threshold set in the patient device 102 (or otherwise triggered an alarm condition), the patient device 102 can send an alarm over the network 109 to the MMS 110. In turn, the MMS 110 can send the alarm or a message representing the alarm to the nurse's station systems 106 and/or the clinician devices 104.

In another embodiment, the patient devices 102 have network capability that enables the patient devices 102 to send the alarm notifications directly over the network 109 to the nurse's station systems 106 and/or to the clinician devices 104. Further, the patient devices 102 may send other types of alarms to the MMS 110, the nurse's station systems 106, and/or the clinician devices 104. Such alarms can include nonclinical alarms that may not represent that a physiological parameter has exceeded a threshold but instead may include information about a sensor that has been disconnected or otherwise has fallen off (often referred to as a probe-off condition). Likewise, a brief power outage or surge can cause the patient device 102 to reset and send a nonclinical alarm to the other devices shown. Such nonclinical alarms are sometimes referred to herein as alerts to distinguish from alarms that may be clinically actionable.

Advantageously, in certain embodiments, the notification client 108 can enable two-way communication with the patient devices 102 and the MMS 110 (and/or the nurse's station systems 106) in the event of an alarm. For instance, an alarm sent from a patient device 102 through the network 109 to the MMS 110 could be routed to the clinician device 104. The notification client 108 can receive this alarm and respond back to the MMS 110 or any other component of the computing environment 100, replying that the message was received. This provision of a reply to the alarm made by the notification client 108 can enable the MMS 110 to determine whether to escalate the alarm or not. Since the MMS 110 has received the indication that the notification client 108 received the message, the MMS 110 may determine to wait a period of time before escalating the alarm to an escalated condition (which will be described in greater detail below).

Alternatively, if the notification client 108 does not respond indicating that the client device 104 has received the alarm message, the MMS 110 may determine that some error (whether of the network 109, the clinician device 104 or otherwise) has caused the clinician device 104 to not receive the message. As a result, the MMS 110 can immediately or otherwise rapidly escalate the alarm to one or more other clinicians without having to wait a set period of time.

Thus, the two-way communication ability of the clinician device 104 can facilitate this rapid escalation because the MMS 110 can assume that if a response is not provided by the notification client 108, that the clinician device 104 likely did not receive the alarm. In an embodiment, the MMS 110 can have high confidence in this conclusion because the clinician device 104 may be locked in software or at the operating system level (e.g., in a kiosk mode or the like) so that users can access only the notification client 108 (and optionally admit module 112 or vital signs verification component 114). Accordingly, no other application access by the clinician may prevent the clinician from viewing notifications from the notification client 108, in an embodiment, resulting in a logical conclusion at the MMS 110 that if the clinician device 104 does not respond, the clinician (or device 104) did not receive the message. Thus, the clinician device 104 may be limited in software to running the notification client 108 (and optionally admit module 112 or vital signs verification component 114) and/or to some other whitelisted set of applications, such as a phone call application, a texting application, a calendaring application, or the like. Additional applications may also be whitelisted or approved to run on the clinician device 104, for example, by a provider of the notification client 108 or by the hospital organization or staff. Many other example benefits of the notification client 108 are described in much greater detail below.

For convenience, this specification primarily describes alarms as being routed through the MMS 110 to the notification client 108 and corresponding response messages being sent from the notification client 108 to the MMS 110 and optionally on to the patient devices 102. However, in other embodiments the notification client 108 can communicate directly with the patient devices 102 or nurse's station systems 106.

As described above, in the depicted embodiment, the clinician device 104 also includes an admit module 112 and a vital signs verification component 114. The admit module 112 is optional in some embodiments. Alternatively, the clinician device 104 may include the admit module 112 without including the notification client 108.

The admit module 112 may include a scanner application or the like that can scan a patient tag and a device tag, obtain identifiers from each tag, and couple the tags in physical computer storage (such as in an electronic medical records system). The tags may be machine-readable codes in the form of barcodes, quick response (QR) codes, radio-frequency identifiers (RFID), combinations of the same, or the like. Further, the admit module 112 may also include functionality for associating the patient with a location such as a room, bed, bassinet (for infants), or the like. Example embodiments of the admit module 112 are described in greater detail below with respect to FIGS. 18 and 19.

The vital signs verification component 114 can include functionality for initiating a vital signs submission process for an admitted patient. Once a patient has been admitted (or optionally thereafter), vital signs can be captured by the patient device and/or by the clinician and submitted via the patient device to a server system for inclusion in the patient's electronic medical record. The vital signs verification component 114 is described in more detail below with respect FIGS. 26 through 28.

III. Example Multi-Patient Monitoring System Features

Figure 2:
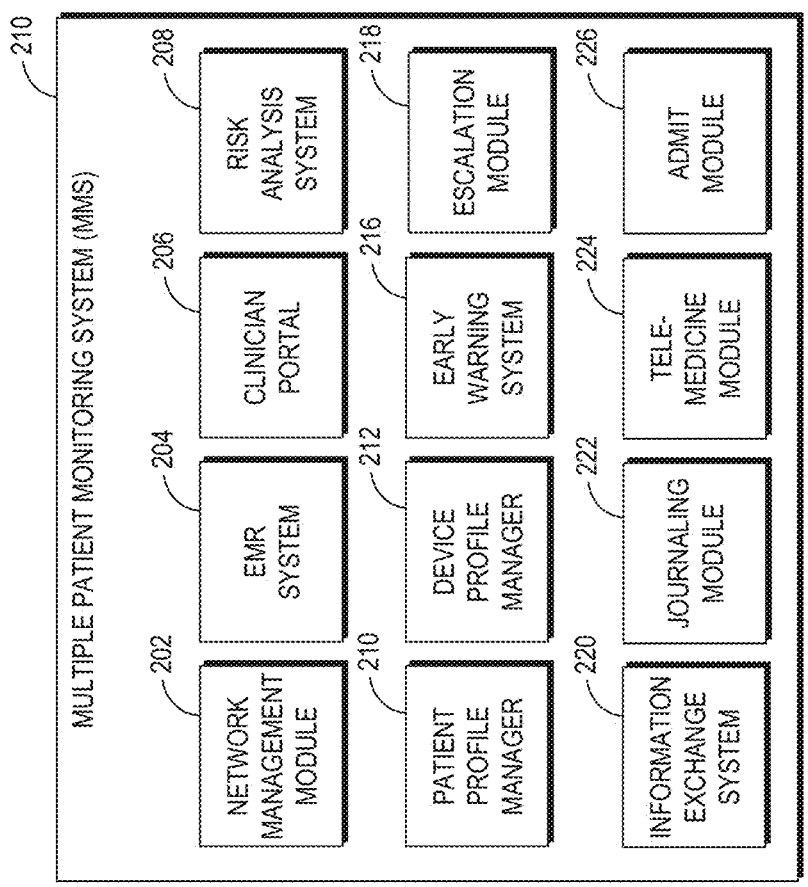
FIG. 2 depicts a more detailed embodiment of the multi-patient monitoring system of FIG. 1.

Turning to FIG. 2, a more detailed embodiment of a multi-patient monitoring system (MMS) 110 is shown, namely, an MMS 210. The MMS 210 can have all of the features of the MMS 110 described above. In the depicted embodiment, the MNS has several subsystems or modules that can be implemented in hardware and/or software. The example modules or components shown group functionality of embodiments of the MMS 210 together under logical descriptions. It should be understood, however, that the various modules and systems shown in the MMS 210 or portions thereof could be implemented together in a single system. In addition, not all of the systems or modules shown need be implemented on the same computing device but could instead be implemented in separate computing devices. Further, some of the modules shown may be omitted in various embodiments.

Certain aspects of the MMS 210 are described as being implemented across multiple clinical facilities. However, the MMS 210 may be implemented in a single clinical facility in other embodiments, and thus, some of the features described herein may be less applicable or not applicable at all to a single-facility installation of the MMS 210. More detailed example features of the MMS 210, any of which may be combined with the features described herein, are disclosed in U.S. application Ser. No. 14/030,360, filed Sep. 18, 2013, titled "Intelligent Medical Network Edge Router" ("the '360 application"), the disclosure of which is hereby incorporated by reference in its entirety and which is included as an Appendix hereto.

The MMS 210 includes, for example, a network management module 202. The network management module 202 can manage network communications with other networks, including networks in hospitals and other facilities as well as communications with mobile patient devices and clinician devices. For example, the network management module 202 can communicate with devices in hospitals and outside of hospitals, or inside of facilities and outside of facilities. The network management module 202 can provide networking services such as load balancing, failover, and the like. In addition, if a patient is monitored in a facility that communicates with the network management module 202, and then the patient is discharged from the facility, the network management module 202 can maintain connectivity with a body-worn or other mobile medical device associated with the patient, for example, over cellular or Wi-Fi links.

The MMS 210 also includes an EMR system 204 that can generally store patient data from any facility, including data collected from patient monitoring devices in patients' homes or while patients are mobile outside of their homes or out of facilities. For example, the EMR system 204 can include such information as parameter values, trend values, alarm histories, patient demographic data, patient condition data including diagnoses, patient medical histories, and patient medications, among a variety of other patient data. The data in the EMR 204 can advantageously be used by other components of the MMS 210 as described below to improve patient care. The EMR system 204 can also store data received from the vital signs verification component 114 described above and in more detail below with respect FIGS. 26 through 28.

A clinician portal 206 of the MMS 210 can provide a user interface or user interfaces that can be accessed by clinicians via their clinician devices to monitor the health status of their patients for whom they are responsible. The clinician portal 206 may, for example, be implemented in one or more web pages, mobile applications, or other network applications and may provide information about the wellness or relative wellness of each patient.

In one embodiment, a wellness score or index is computed for some or all patients by a risk analysis system 208 of the MMS 210, and the clinician portal 206 can depict these wellness indices among other parameter data, trend data and alarms for each patient. In one embodiment, the clinician portal 206 facilities triaging patients by providing functionality for patients to be ordered or ranked based on their wellness scores or indices as computed by the risk analysis system 208. Example features for computing wellness indices or risk assessments and which may be implemented herein are described in U.S. application Ser. No. 13/269,296, filed Oct. 7, 2011, titled "Risk Analysis System," and Ser. No. 13/371,767, filed Feb. 13, 2012, titled "Medical Characterization System," the disclosure of which is hereby incorporated by reference in its entirety. For example, the risk analysis system 208 can take into two or more parameters, such as any combination of the following parameters: oxygen saturation (e.g., $SpO_2$), respiratory rate, pulse rate, heart rate, total hemoglobin level, methemoglobin, carboxyemoglobin, blood pressure, ECG output, encephalography output, or the like. The risk analysis system 208 can combine data from such parameters and reduce this data to a single value or data representation of the combination of those parameters. The single value may be, for example, an index or score that is on a scale of 0 to 10, where 10 may represent a most healthy state, while 0 may represent a least healthy state. Thus, such scores could be used to rank the relative health state or acuity of patient sicknesses and such numerical rankings can be output for presentation to clinicians in the clinician portal 206, thereby enabling clinicians to quickly triage patients.

In some embodiments where the MMS 210 is implemented for multiple clinical facilities, the risk analysis system 208 also leverages aspects of the cloud-based infrastructure of the MMS 210 to improve the wellness index calculation. For example, the risk analysis system 208 may be able to access patient profile data from the MMS 210 that comes from previous hospital visits or other clinical facility visits from a single facility or multiple facilities to compute historical wellness indices or to compute a current wellness index. The risk analysis system 208 can also personalize the wellness index based on patient attributes stored in the EMR system 204. For example, the risk analysis system 208 can personalize which parameters are weighted more heavily in the combination of parameters that are output as a wellness index based on previous patient conditions listed in EMR system 204. In currently available systems, different institutions typically do not share their EMR data, and EMRs therefore cannot be used to correlate patient data from multiple institutions together and thereby improve risk analysis and wellness indices. However, such advantages can be made possible in certain embodiments by the centralized cloud nature of the MMS 210.

The MMS 210 also includes a patient profile manager 211. The patient profile manager 211 can manage patient profiles, which can include information about patient demographics, patient alarm settings, including alarm settings from previous visits to potentially multiple different facilities, patient conditions and so forth, and example features of which are described in greater detail below with respect to FIG. 3. The MMS 210 further includes a device profile manager 212 that can manage and store device profiles for medical devices that interact with the MMS 210 as well as optionally other computing devices. The profiles may have information about rules that can be used to track the usage of these devices as well as a variety of other features.

The MMS 210 also includes an early warning system 216. The early warning system 216 can issue early warning alarms based on parameter measurements, indices such as the wellness index or other indices. The early warning system 216 can look for patterns in patients to facilitate detecting never events, including events that should occur never or rarely, like a patient dying in bed without any intervention, particularly when a patient is home and would not ordinarily be under the care of a hospital or have access to a system like the risk analysis system 208 or the early warning system 216.

An information exchange system 220 of the MMS 210 can facilitate communicating information about patients to government or research institutions 118 described above with respect to FIG. 1. One scenario where patient information may be submitted (anonymously) to government or research institutions is where a disease outbreak has occurred. For example, information may be provided that indicates several patients in a hospital have come down with the flu. The information exchange system 220 can report this occurrence to an external entity such as the CDC or the Center for Disease Control, or state or local government agency or national government agency or worldwide agency to alert such agencies other institutions of the potentiality of a disease outbreak. If multiple institutions are using the services of the MMS 210, then such information about patient conditions can be correlated and provided to these institutions as described above. More generally, the information exchange system 220 can provide data about changing patient conditions continuously or periodically to government or research organizations to enable such organizations to rapidly respond to changes in regional health issues.

Further, the data provided by the information exchange system 220 can be valuable to government agencies or research institutions to determine the effects of local conditions on health conditions. It may be discovered, for instance, that patients that go to a specific facility or set of facilities in a region are afflicted with disease related to nearby coal mining which can be ascertained by research institution or a government agency that has responsibility over such activities. Accordingly, the information exchange system 220 can provide value data that can provide reports that can be used by external entities to improve patient care.

A journaling module 222 of the MMS 210 can capture clinician interactions with medical devices that are in the institutions and/or that are in patients' homes or that are body worn in mobile situations. The interactions can include any type of button press, alarm setting change, machine-readable code (e.g., 1-D or 2-D barcode) or RFID tag interaction, or the like and can be recorded for the purposes of determining clinician response times to alarms or other measures of the quality of a clinician's care. The journaling module 222 can further leverage the centralized monitoring capabilities of the MMS 210 to compare the quality of care as journaled or otherwise calculated amongst different institutions as an apples-to-apples comparison because some or all of the data from these institutions can be provided to the centralized MMS 210.

Further, the journal module 222 can facilitate comparing the quality of care between different units in a hospital or other facility including different floors or groups of clinicians or shifts, or the like. The journal module 222 can also facilitate comparing similar groups amongst different facilities, such as an ICU group in two different facilities, and can thereby enable an organization to identify gaps or deficiencies of care in different facilities that can be corrected. This information can be provided in real time or near-real time so that adverse patient care outcomes can be quickly addressed, in contrast to the past where information about quality of care is often analyzed well after an adverse care event has occurred (or even after a patient has been discharged). Further embodiments of journaling and detecting clinician interactions with devices (including via RFID tags) are described in U.S. application Ser. No. 14/032,132, filed Sep. 19, 2013, titled "Medical Monitoring System" ("the '132 application"), the disclosure of which is hereby incorporated by reference in its entirety.

A telemedicine module 224 of the MMS 210 can facilitate telecommunications between clinicians and patients, including telepresence communications where clinicians can diagnosis, treat, or otherwise attend to the needs of patients remotely using audio visual systems or the like. In some embodiments, the telemedicine module 224 can also be used in conjunction with features of the escalation module 218 described below.

The escalation module 218 can provide functionality for escalating alarms from a first or primary care provider to a second or subsequent care provider in case the primary care provider is unavailable. In certain embodiments, the escalation module 218 can perform escalation as follows (or the like). If an alarm is received from a patient device, the escalation module 218 can initially supply an alarm notification message regarding the alarm to one or more clinician devices 104. These clinician device(s) 104 may correspond to a primary care clinician or group of clinicians who have primary responsibility for the patient for whom the alarm was made. (Any of the alarms described herein, including escalation alarms and reescalation alarms, may be provided to a group of clinicians rather than to a single clinician. However, for ease of explanation, many examples herein use a single clinician in the alarm message.) If no response to this initial alarm message is provided by the clinician device 104 (or the notification client 108 installed thereon), the escalation module 218 can escalate to a second clinician or group of clinicians by sending the alarm notification message to the second clinician or second group of clinicians. This escalation may optionally include sending the alarm notification message to the primary clinician or group of clinicians as well. The alarm notification message may indicate that it is an escalated message to reflect an increased urgency of the alarm.

If no response is provided by the clinician device(s) 104 to the escalation module 218 or, alternatively, if the alarm continues to be provided by the patient device 102 to the escalation module 218, the escalation module 218 can re-escalate. In an embodiment, the escalation module 218 re-escalates by sending the alarm notification message or a similar alarm message to a supervisor such as a charge nurse or an administrator who has responsibility over a group of patients. In addition, this reescalation message may be sent to the first and/or second groups of clinicians as well. The alarm notification message may indicate that it is a re-escalated message to reflect an even greater urgency of the alarm. As used herein, in addition to having its ordinary meaning, "escalation" can include re-escalation. Thus, for example, an alarm may initially be sent, escalated, and escalated again (e.g., re-escalated).

In an embodiment, since the notification client 108 described above can respond to the escalation module 218, the escalation module 218 can manage escalations more intelligently. For instance, the escalation module 218 can detect whether the clinician device has received an alarm notification message, an escalation message, or a re-escalation message. If the message has not been received, the escalation module 218 can escalate or re-escalate the alarm. In addition, if a clinician indicates through the notification client 108 that he or she cannot address the alarm, the escalation module 218 can automatically escalate or re-escalate the alarm. Additional embodiments of interactions between the escalation module 218 and the notification client 108 are described in greater detail below with respect to FIGS. 3 and 4.

As described above, the escalation module 218 can send an initial alarm to a first clinician or group of clinicians, escalate the alarm to a second clinician or group of clinicians, and re-escalate the alarm to a third clinician or group of clinicians. While these groups may be defined before the alarm occurs, in some embodiments, the escalation module 218 uses location-based rules to dynamically select which clinicians to send an alarm to (whether initially or via escalation/re-escalation). The location-based rules can take into account which clinicians are closer to the patient. For instance, the escalation module 218 can initially send an alarm to a clinician closest to a patient, then escalate to clinicians in closer proximity to the patient than other clinicians, and so on.

The escalation module 218 may know the locations or approximate locations of the clinicians because the clinician devices 104 may include location-tracking hardware and/or software that can report their locations to the escalation module 218. The location-tracking hardware and/or software can use triangulation techniques to determine clinician location, for example, by triangulating with wireless access points within a clinical facility (or cell towers to triangulate inside or outside a facility). The location tracking hardware and/or software may instead use global positioning system (GPS) features to track clinician location. Other location-tracking techniques can include dead-reckoning or dead-reckoning combined with any of the above techniques for calibration. In addition, in some embodiments, the escalation module 218 can implement any of the location-based escalation rules or clinician location tracking techniques described in the '132 application, incorporated above.

In other embodiments, the escalation module 218 may send alarms to or escalate to clinicians who are not close by the patient and who may, in fact, be geographically remote from the patient. Send alarms or escalations to such clinicians may be possible because such clinicians can use telepresence or telemedicine techniques to interact with patients. The telemedicine module 224 may provide remote clinicians with access to patient parameter data, trend data, and/or video data, enabling remote clinicians to intervene in at least some alarm situations. In some situations, a remote clinician can instruct a local clinician on techniques to be used to remediate an alarm and care for a patient. For instance, a doctor or specialist may remotely instruct a nurse on how to care for a patient undergoing an alarm condition. The escalation module 218 may use other remote escalation techniques described in the '360 application, incorporated above.

The MMS 210 also includes an admit module 226 in the depicted embodiment. The admit module 226 may communicate with the admit module 112 installed in the clinician device(s) 104. As described above, the admit module 112 in the clinician device(s) 104 may include a scanner application or the like that can scan a patient tag and a device or location tag, obtain identifiers from each tag, and couple the tags in physical computer storage (such as in an electronic medical records system). This coupling can include sending a message from the admit module 112 to the admit module 226. The admit module 226 can receive the patient identifier and device or location identifier(s) from the admit module 112 and associate the identifiers in physical computer storage, such as in the EMR system or another database. For instance, the admit module 226 can create a data record in a database that includes both the patient identifier and a device and/or location identifier. Further, the admit module 226 can receive a clinician identifier from the admit module 112 and store the clinician identifier together with the patient identifier and/or device/location identifier(s). This information may be accessed by the escalation module 218, among other modules, to properly identify which devices, locations, and/or clinicians are associated with a patient so to send alarm notification messages with proper identifying information to the proper clinicians.

IV. Example Alarm Notification Processes

Figure 3:
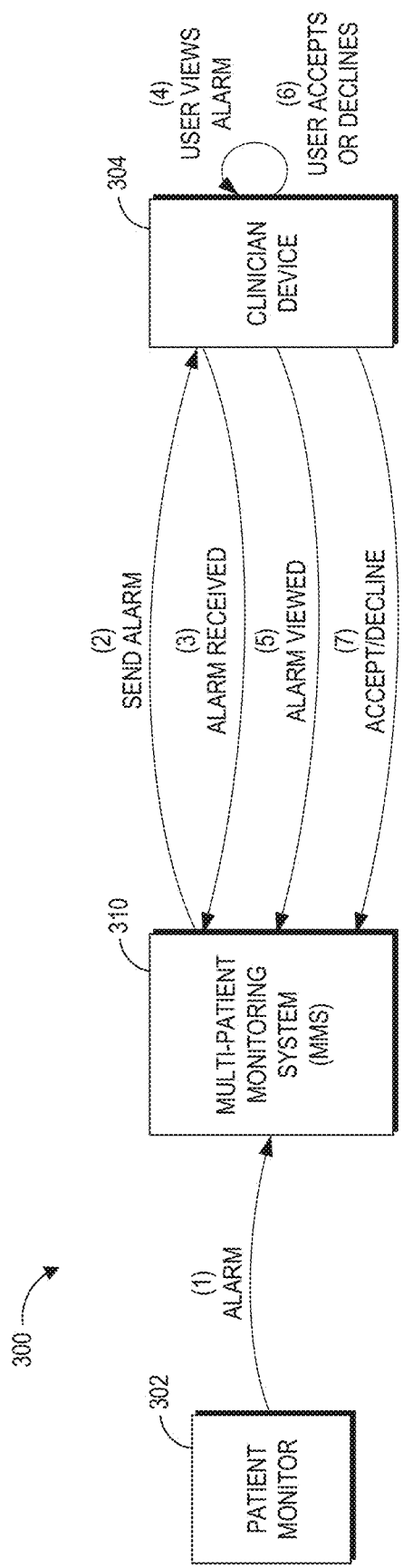
FIG. 3 depicts an example alarm lifecycle flow diagram.

Turning to FIG. 3, an example alarm lifecycle flow 300 is shown. The flow 300 depicts an example state flow of an alarm notification message from a patient monitor 302 to receipt by a clinician device 304. In an embodiment, the lifecycle flow 300 depicts examples of how the clinician device 304 can respond to the alarm so as to improve patient outcomes. The patient monitor 302 is an example embodiment of the patient monitor 102. Likewise, the clinician device 304 is an example embodiment of the clinician device 104. Also shown is a multi-patient monitoring system (MMS) 310, which may have some or all the functionality of the MMS 110 or 210.

In the depicted embodiment, the patient monitor 302 at state 1 issues an alarm to the MMS 310. The alarm may be a clinical alarm or a nonclinical alarm as described above. At state 2, the MMS 310 sends an alarm notification message to the clinician device 304. A notification client (not shown; see FIG. 1) in the clinician device 304 can indicate that the alarm was received at state 3 by providing a return message to the MMS 310. As a result, the MMS 310 can know that the alarm was received by the clinician device 304 and therefore justifiably wait a period of time to escalate. In contrast, if the alarm had not been indicated as being received by the clinician device 304 to the MMS 310, the MMS 310 may rapidly escalate (see, e.g., FIG. 4).

At state 4, a user of the clinician device 304 may view the alarm using, for example, the notification client 108. The user may view the alarm in a variety of ways. Generally speaking, the notification client 108 can depict a user interface that shows some aspect of the alarm on a lock screen of the notification client 108, on an active alerts screen, or on an application screen of the notification client 108. The notification client 108 may consider the alarm as being viewed if the clinician device 304 changes state from locked to unlocked (e.g., via button press by the clinician) and if the lock screen depicts the alarm (see, e.g., FIG. 5 below). In another embodiment, the notification client 108 considers the alarm as being viewed if the clinician unlocks the lock screen and views a list of alarms including this particular alarm (see, e.g., FIG. 6). In another embodiment, the notification client 108 considers the alarm as being viewed if the clinician unlocks the lock screen, views a list of alarms including this particular alarm, and then selects this particular alarm (see, e.g., FIG. 7).

At state 5, the clinician device 304 reports to the MMS 310 that the alarm has been viewed. This state may also be implemented by the notification client 108 by reporting that the alarm has been viewed. The notification client 108 of the clinician device 304 can enable the MMS 310 to know that the clinician is now aware of the alarm and not just that the clinician's device 304 has received the alarm. Knowing (or, equivalently, receiving or storing an indication in the MMS 310) that the clinician has viewed the alarm can further increase confidence that the clinician may respond to the alarm. Conversely, if the alarm had been received by the clinician device 304 but had not been indicated as being viewed by the clinician, the MMS 310 might hasten escalation to another clinician or set of clinicians (see, e.g., FIG. 4).

At state 6, the user can accept or decline to handle the alarm, for example, by inputting an indication of acceptance or declining to the clinician device 304. The notification client 108 may, in some embodiments, infer the clinician's decision to accept handling or decline handling the alarm based on the user's input. For instance, if the clinician marks an alarm notification message as "unread" (e.g., similar to marking an email as unread), then the notification device client 108 may infer that the clinician has decided not to handle the alarm. At state 7, the clinician device 304 reports to the MMS 310 whether the clinician has decided to accept or decline the alarm. If the clinician has declined to handle the alarm, the MMS 310 can rapidly or immediately escalate the alarm to another clinician or set of clinicians.

In one embodiment, acceptance is not provided as an option in the notification client 108 because a clinician may directly respond to the alarm without indicating his acceptance of the alarm. Likewise, many other aspects described herein are optional and may be omitted or added thereto in other embodiments.

Figure 4:
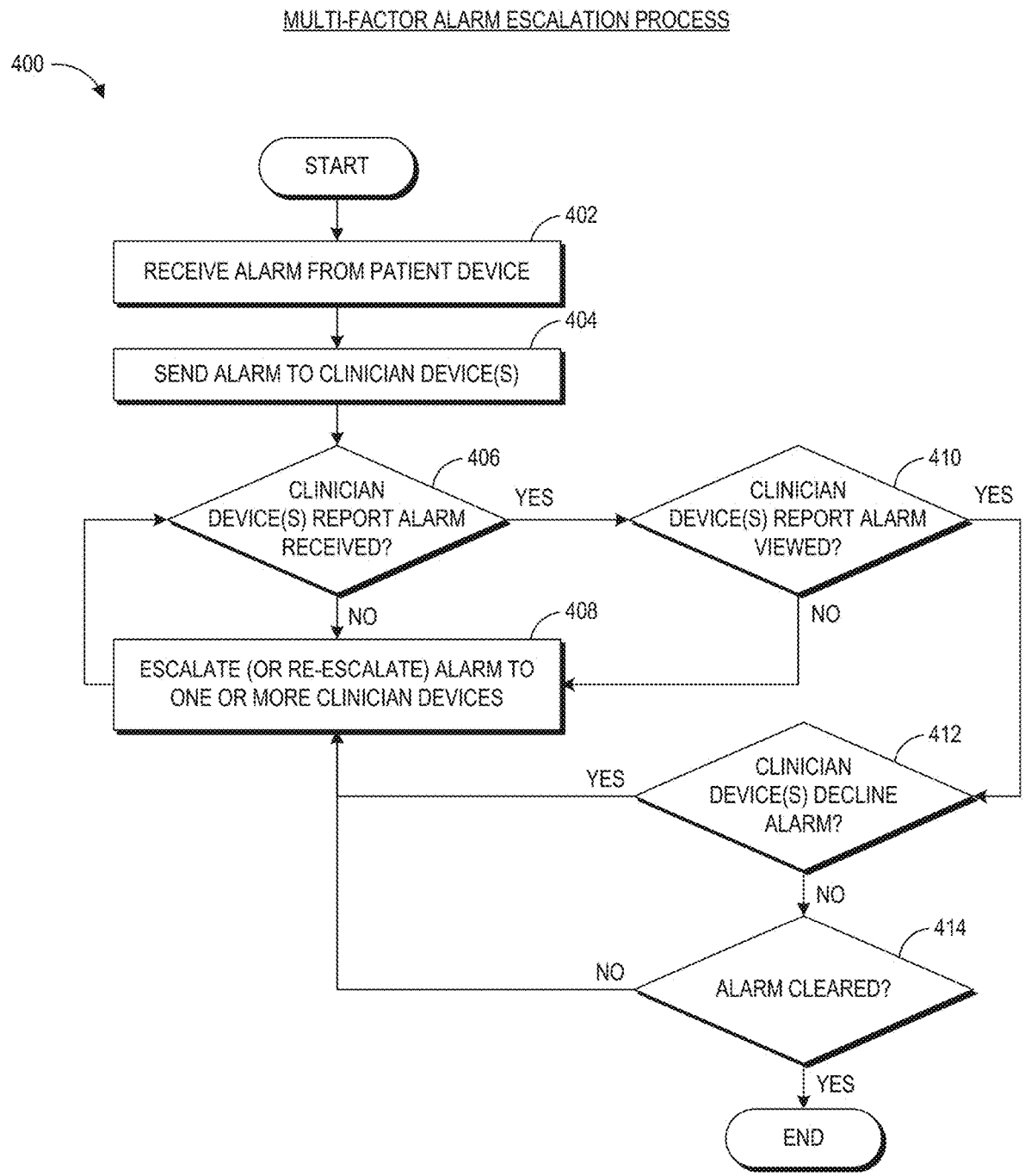
FIG. 4 depicts an embodiment of a multi-factor alarm escalation process.

Turning to FIG. 4, an embodiment of a multi-factor or two-way alarm escalation process 400 is shown. The alarm escalation process 400 may be implemented by any of the systems described herein including the MMS 110, MMS 210, or MMS 310. For convenience, the alarm escalation process 400 will be described in the context of the escalation module 218 of the MMS 210, although other computing systems not described herein may implement the alarm escalation process 400. In certain embodiments, the alarm escalation process 400 can advantageously provide improved patient outcomes by more rapidly responding to alarms via escalation due to the two-way nature of the alarm message lifecycle described herein.

At block 402, the escalation module 218 receives an alarm from a patient device and sends the alarm to a clinician device or devices at block 404. At decision block 406, it is determined by the escalation module 218 whether the clinician device or devices report the alarm having been received. If not, at block 408, the escalation module 218 escalates the alarm to one or more other clinician devices, which may but need not include the initial clinician device or devices to which the initial message was sent.

In an embodiment, if the initial message was sent to a single clinician device and at block 406 it is determined that the clinician device did not report receiving the message, escalation happens automatically at block 408. In another embodiment, when the initial message is sent to a plurality of clinician devices, block 406 does not trigger escalation at block 408 until it is determined that none of the clinician devices reported receiving the alarm. Alternatively, the escalation module 218 can implement a hybrid approach where if any of a plurality of client devices have not responded as receiving the message, the escalation module 218 can escalate at block 408. In another embodiment, the escalation module 218 escalates if a majority of the client devices did not receive the alarm or indicate having received the alarm message. Other embodiments are possible.

If, at decision block 406, the clinician device or devices reported receiving the alarm, then it is further determined by the escalation module 218 at block 410 whether the clinician device or devices reported the alarm being viewed by a user. If not, then the escalation module 218 can escalate or re-escalate the alarm at block 408 to one or more clinician devices. As used herein, in addition to having its ordinary meaning, the term "re-escalate" can refer to escalating a second time or any successive time after a previous escalation has occurred.

As with the decision block 406, the decision block 410 can select a different output depending on the number of clinician devices to which the alarm was sent. If a plurality of clinician devices received the alarm, then the escalation module 218 may proceed to block 408 and escalate if just one of them did not indicate that the user viewed the message. In another embodiment, escalation occurs at block 408 if a majority did not view the message, or if all did not view the message, or the like.

If the clinician device or devices reported the alarm being viewed at block 410, the process 400 proceeds to block 412. At block 412, the escalation module determines whether the clinician device or devices declined the alarm. If the clinician device or devices declined the alarm, then the escalation module 218 proceeds to escalate or re-escalate at block 408. As with the previous decision block 406 and 410, the escalation may occur at block 408 via block 412 if a single device declined the alarm or if a majority or all of the devices declined the alarm, depending on the implementation. If one or more devices did not decline the alarm at block 412, then the escalation module 218 awaits to determine whether the alarm has been cleared at block 414. If the alarm has been cleared, the process 400 ends; otherwise, the escalation module 218 escalates or re-escalates at block 408.

In certain embodiments, if multiple parameters are alarming at the same time or together (e.g., one after another and the first has not yet been cleared by clinician or on its own), the process 400 may be modified. For instance, any step in the process may be truncated in time, e.g., by shortening wait times, to escalate faster at any point in the process 400.

V. Example Alarm Notification User Interfaces

FIGS. 5 through 17 depict several example user interfaces that may be implemented in a clinician device 504. The user interfaces shown depict example output of the notification client 108 described above and may be implemented in any of the clinician devices described herein. The example clinician device 504 shown in FIGS. 5 through 17 may have any of the features of the clinician devices described above.

The user interfaces shown may be implemented in a mobile application such as an application that runs on a mobile operating system such as the Android™ operating system available from Google™ or the iOS™ operating system available from Apple™. Alternatively, or in addition to being a mobile application, the user interfaces shown can be implemented in a web application that runs in a browser. Thus, the notification client 108 may be a mobile application or may be a browser, or in some embodiments, may include the functionality of both.

The user interfaces shown are merely examples that illustrate some example embodiments described herein and may be varied in other embodiments. For instance, user interface controls shown may include buttons, touch-selective components and the like which may be altered to include any type of user interface control including, but not limited to, checkboxes, radio buttons, select boxes, drop-down boxes, textboxes or any combination of the same. Likewise, the different user interface controls may be combined or their functionality may be spread apart amongst additional controls while retaining the similar or same functionality as shown and described herein with respect to FIGS. 5 through 17. Although touchscreen interfaces are shown, other clinician devices may implement similar user interfaces with other types of user input devices such as a mouse, keyboard, stylus, or the like.

Figure 5:
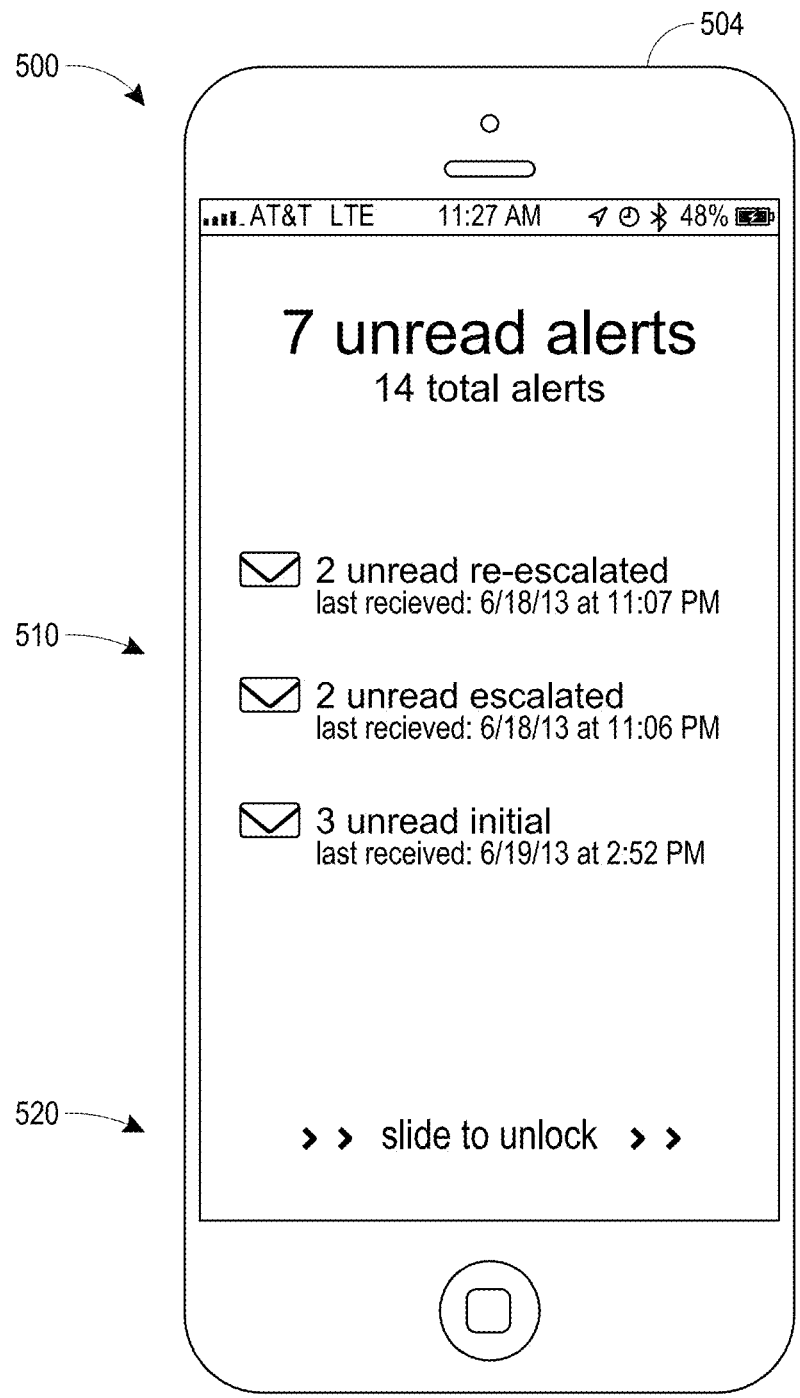
FIGS. 5 through 17 depict example clinician device user interfaces.

Turning specifically to FIG. 5, the clinician device 504 is shown depicting a lock screen user interface 500. The lock screen user interface 500 may be shown when the clinician device 504 comes out of a sleep mode or is otherwise unlocked by a user. The lock screen user interface 500 may be displayed, for instance, if the user presses a power button on the device 504 or if the device 504 receives an alarm notification.

The example lock screen user interface 500 shows lock screen notifications 510 which, in the depicted example, list three unread initial alarms, two unread escalated alarms, and two unread re-escalated alarms. In an embodiment, these alarms can be output by the notification client 108 to the lock screen. A user may select an unlock mechanism 520 on the lock screen user interface 500 to unlock the clinician device 504 and be presented with other user interfaces such as a user interface 600 shown in FIG. 6.

Figure 6:
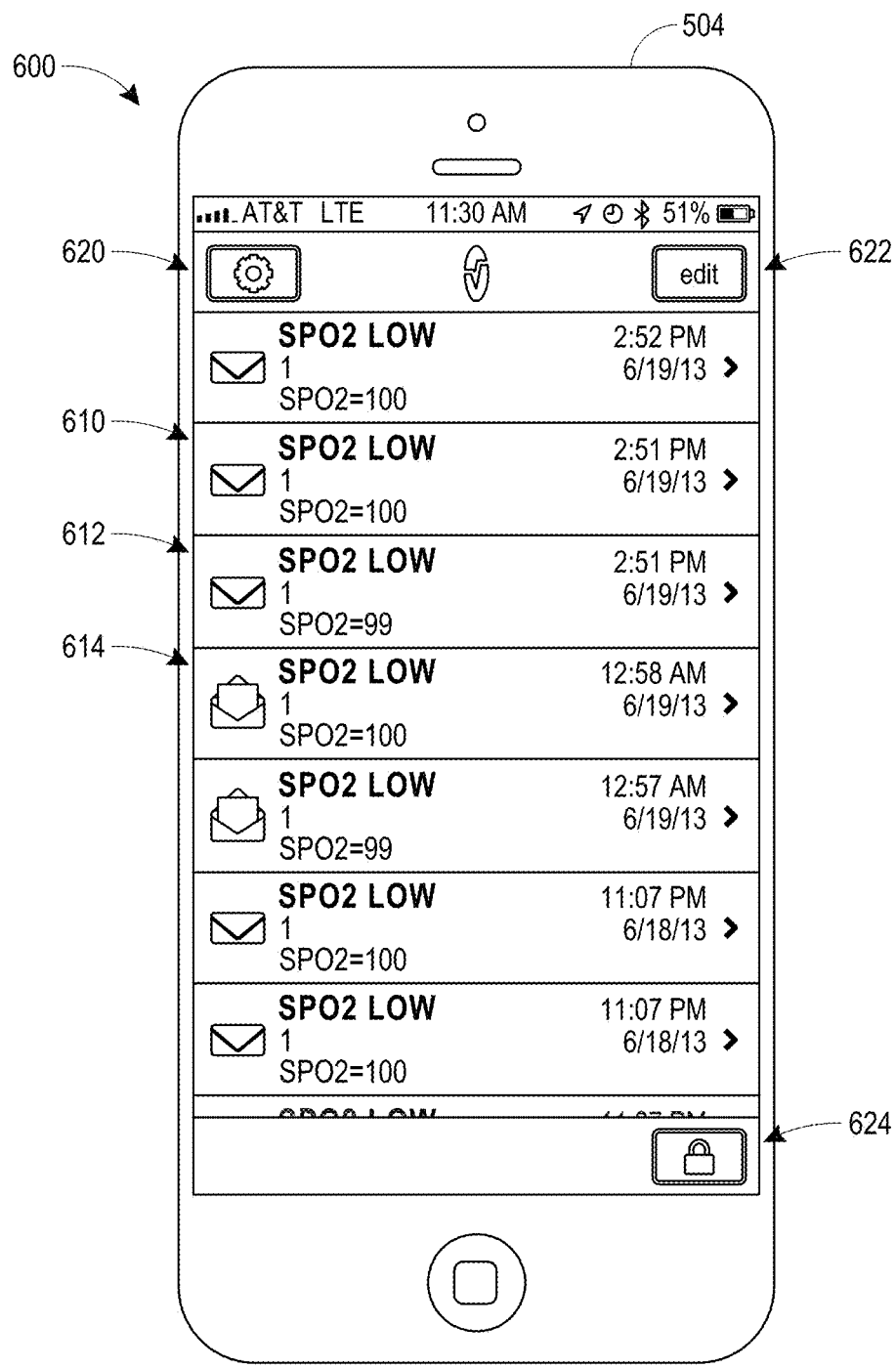

With reference to FIG. 6, the user interface 600 depicts a list of example alarm notifications 610 in more detail. Each notification 610 includes, in the depicted embodiment, information about the type of the alarm, whether it is an initial alarm, escalation, or reescalation; information about the patient, including the patient's identifier such as a room number of the patient; the time and date of the alarm; the parameter value associated with the alarm; and the like. An alarm type icon 612 shown next to each notification 610 can indicate the type of alarm whether it be an initial alarm, an escalation alarm, or a re-escalated alarm. The alarm type icon 612 is an envelope in the depicted embodiment and may be a different color depending on the type of the alarm. For instance, the alarm type icon 612 can be blue for an initial alarm, yellow for an escalated alarm, and red for a re-escalated alarm to indicate the degree of severity of those alarms, although other colors may be chosen. Another icon 614 depicts an open envelope, indicating that the notification has already been viewed by the user.

Other user interface elements may be chosen to indicate whether the alarm is an initial, escalation, or reescalation alarm. For example, the type of alarm may be spelled out with text in the user interface 600 as an initial, escalation, or reescalation alarm. The alarm might be indicated as the "1st" alarm, "2nd" alarm, or "3rd" alarm with numbers or the like, or with letters such as A, B, C, and the like. Further, an abbreviation such as "I" for initial, "E" for escalation, and "R" for reescalation may also be displayed. Although three different types of alarms are described herein, it should be understood that one or more additional levels of escalation may be displayed. Alternatively, there may be fewer than three levels of alarms, such as just an initial alarm and an escalated alarm.

Other options shown include a settings control 620 that enables a user to affect settings of the notification client. Selection of the settings control 620 can cause the user interface shown in FIG. 15 to be displayed, which is described in detail below. In addition, an edit control 622 is shown that enables deleting old notification 610. Selection of the edit control 622 can cause user interfaces such as are described below with respect to FIGS. 13 and 14 to be displayed. A lock control 624 is also shown that enables the user to put the client device 504 in a lock state, outputting a user interface such as the lock screen user interface 500 of FIG. 5.

Figure 7:
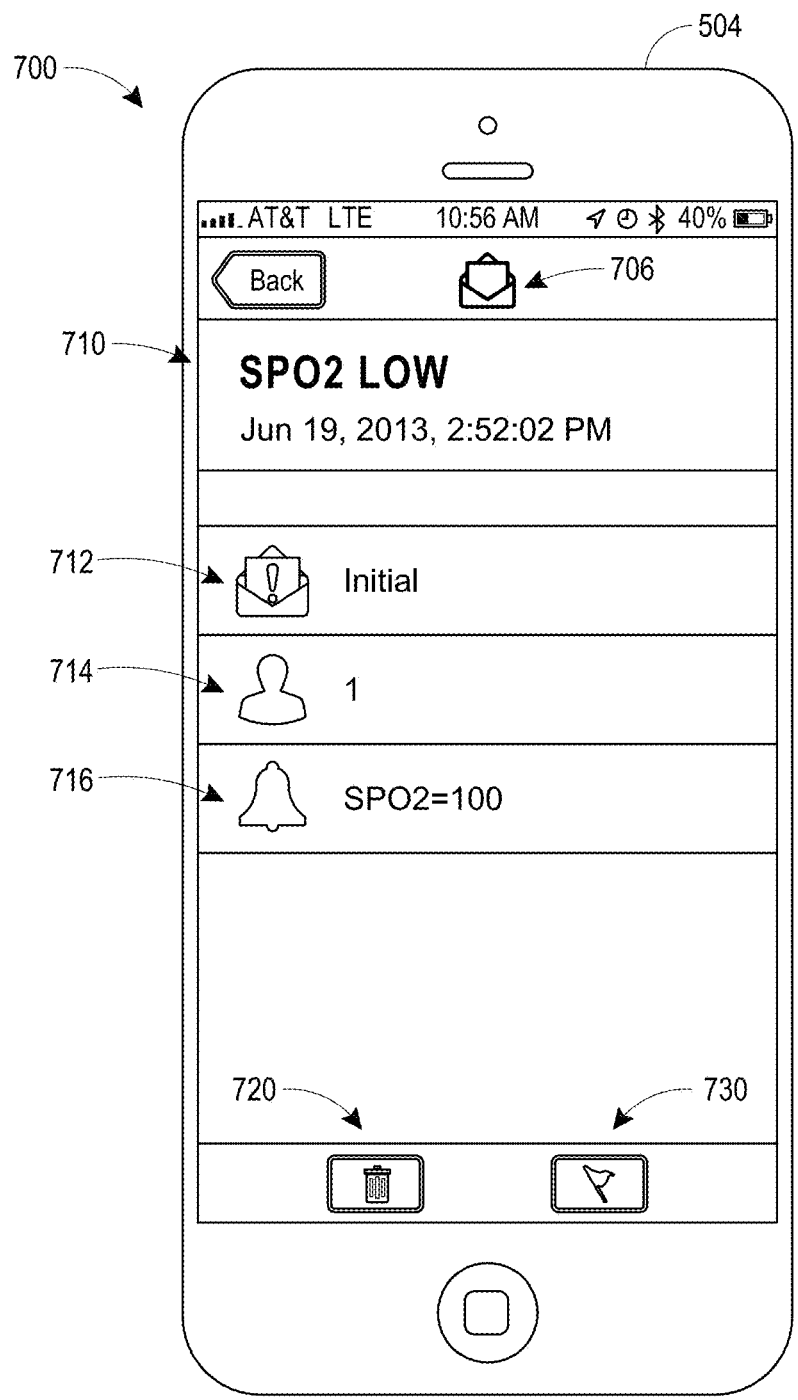
Figure 8:
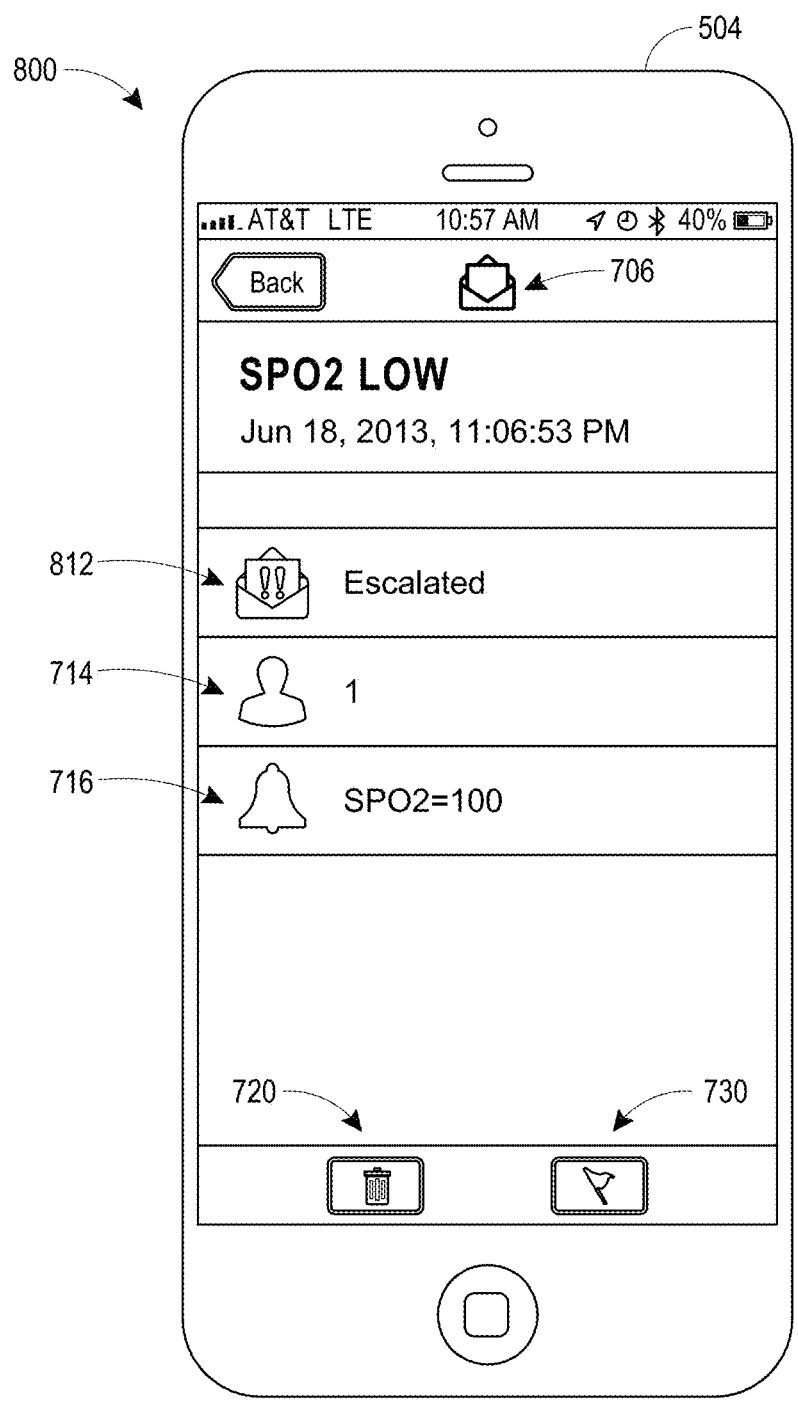
Figure 9:
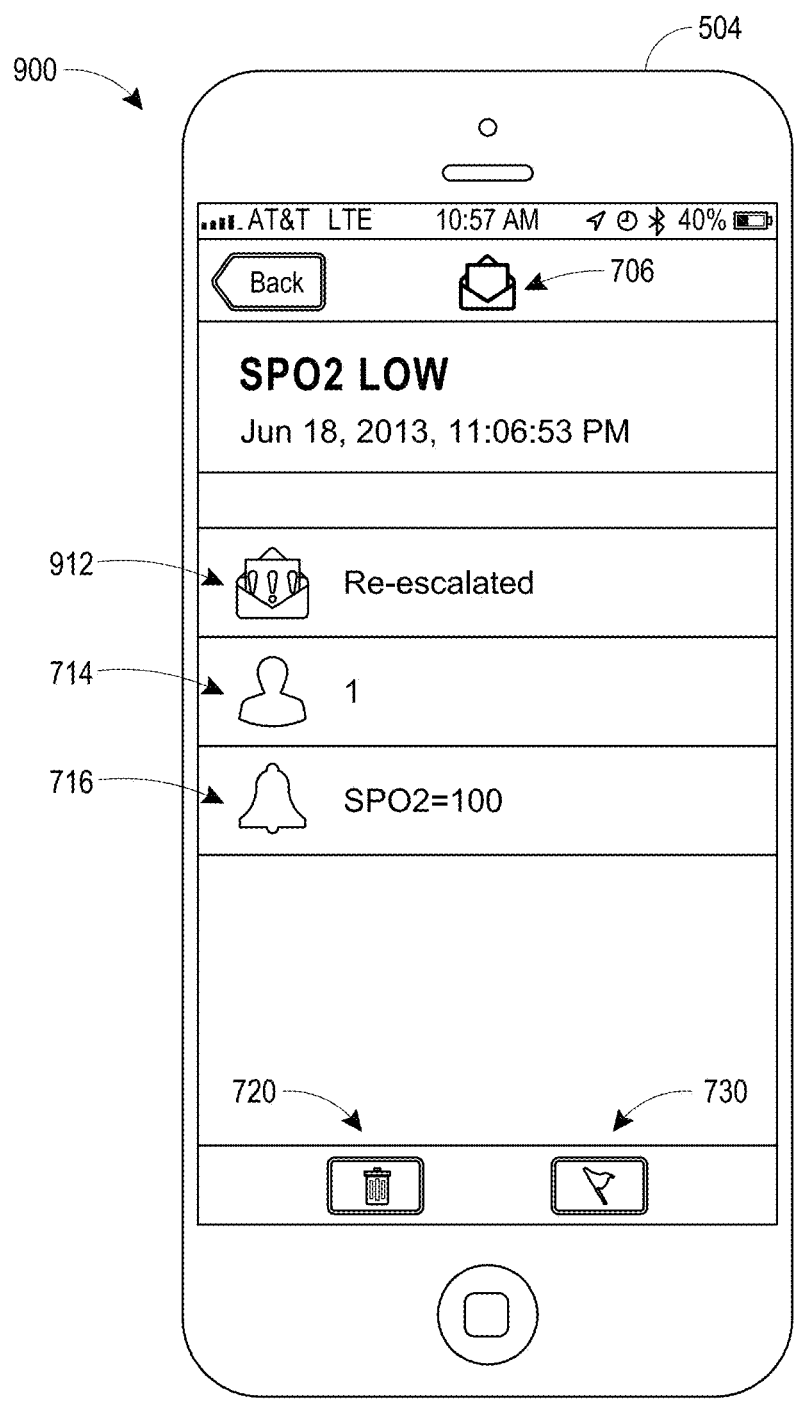

Selection of any of the notifications 610 can cause user interfaces such as the user interfaces 700, 800 or 900 of FIG. 7, 8, or 9, respectively, to be displayed. FIG. 7 in particular depicts a user interface 700 for an initial alarm notification, FIG. 8 depicts a user interface 800 of an escalated alarm notification, and FIG. 9 depicts a user interface 900 of a re-escalated alarm notification.

With specific reference to FIG. 7, the user interface 700 includes information about the notification 710, a message read icon 706 indicating that the message has been opened, a notification type icon 712 that indicates that this is an initial alarm, and a room number 714 and a parameter value 716, which in this is depicted by SpO2. In an embodiment, the user can select the parameter value to see additional details about the user including a trend of the parameter value 716 over time, other historical data, or the like. In addition, other user interface controls may be provided in the user interface 700 (or 800 or 900) to access this trend and more detailed parameter information. Further, a user interface control may be provided for accessing a video of the user as described in greater detail below. Other controls, including a control 720 for deleting the message and a control 730 for marking the message unread are also shown. Selecting the control 730 can cause the user interface shown in FIG. 10 to be displayed, which will be described in greater detail below.

Turning to FIG. 8, many of the same features described with respect to FIG. 7 are shown with the difference that the notification type icon 812 is an escalated type icon. Likewise in FIG. 9, similar features are shown as in FIGS. 7 and 8 except that a notification type icon 912 indicates that this is a re-escalated alarm.

Figure 10:
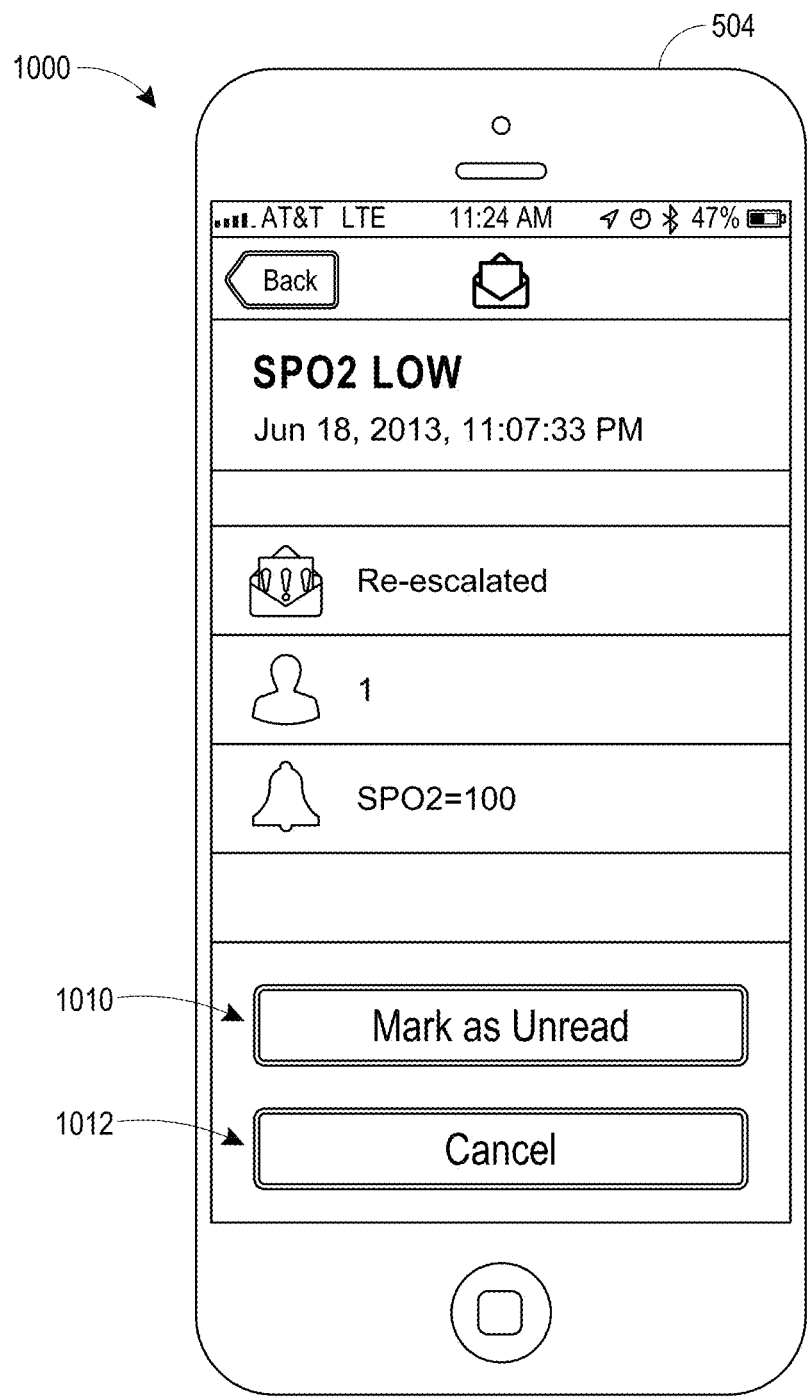

Turning to FIG. 10, selection of the mark unread control 730 from FIG. 7, 8 or 9 can cause the user interface 1000 to be shown. The user interface 1000 includes a button 1010 to confirm that the message is to be marked unread as well as a button 1012 to cancel the marking of the message being unread. If the message is marked unread, then the notification client 108 can send a message to the MMS that indicates that the clinician has declined to handle this alarm. The MMS can then use this message to automatically escalate rapidly unless perhaps other members of the team have not yet marked their messages unread (see FIG. 4).

Figure 11:
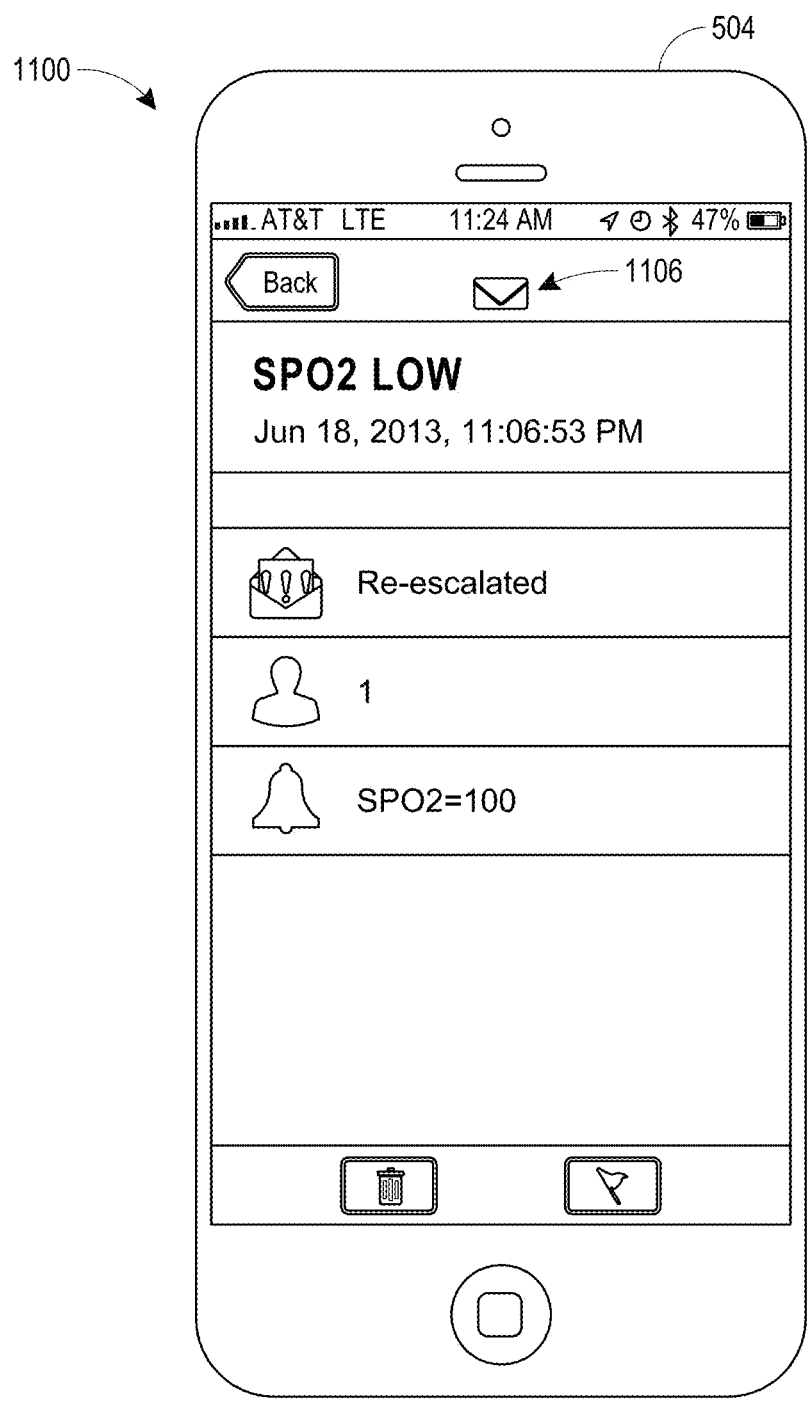

Marking the message as unread can cause a user interface 1100 shown in FIG. 11 to be shown which is similar to the user interfaces 700, 800 and 900 except that the user interface 1100 includes a message unread icon 1106 at the top of the user interface 1100.

Figure 12:
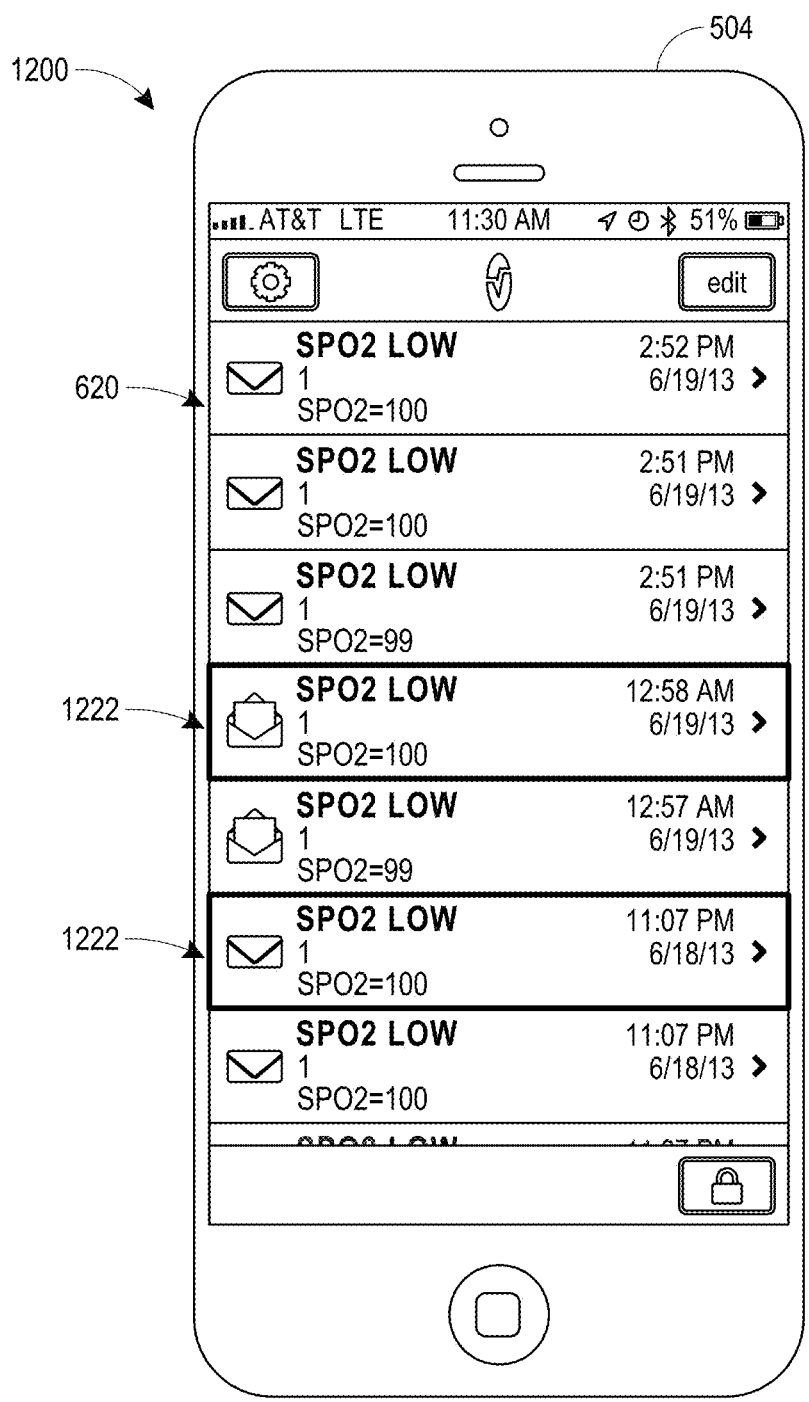

FIG. 12 shows a user interface 1200 that is another view of the user interface 600 of FIG. 6, including the notifications 620 described above as well as alarm cleared indicators 1222. The alarm cleared indicators 1222 are, in the depicted embodiment, boxes that surround a few of the notifications 620 shown. The boxes may be green or some other color that indicates that the alarm has been cleared. Other ways to show that the alarm has been cleared may include making the background color of the notification 620 green or some other color, or graying out the notification 620 for which their alarms are cleared, or collapsing them so that they are no longer visible on the display, or archiving them, for example, by auto-deleting them. However, in an embodiment, auto-deleting notifications when an alarm is cleared can be confusing for a clinician especially since some patients go in and out of alarm states rapidly, which could potentially cause flickering of alarms. Auto-deletion of alarm notifications upon alarm clearance could also cause confusion for clinicians. Thus, alarms are not auto deleted in some embodiments but instead are otherwise marked with their status as being cleared.

Figure 13:
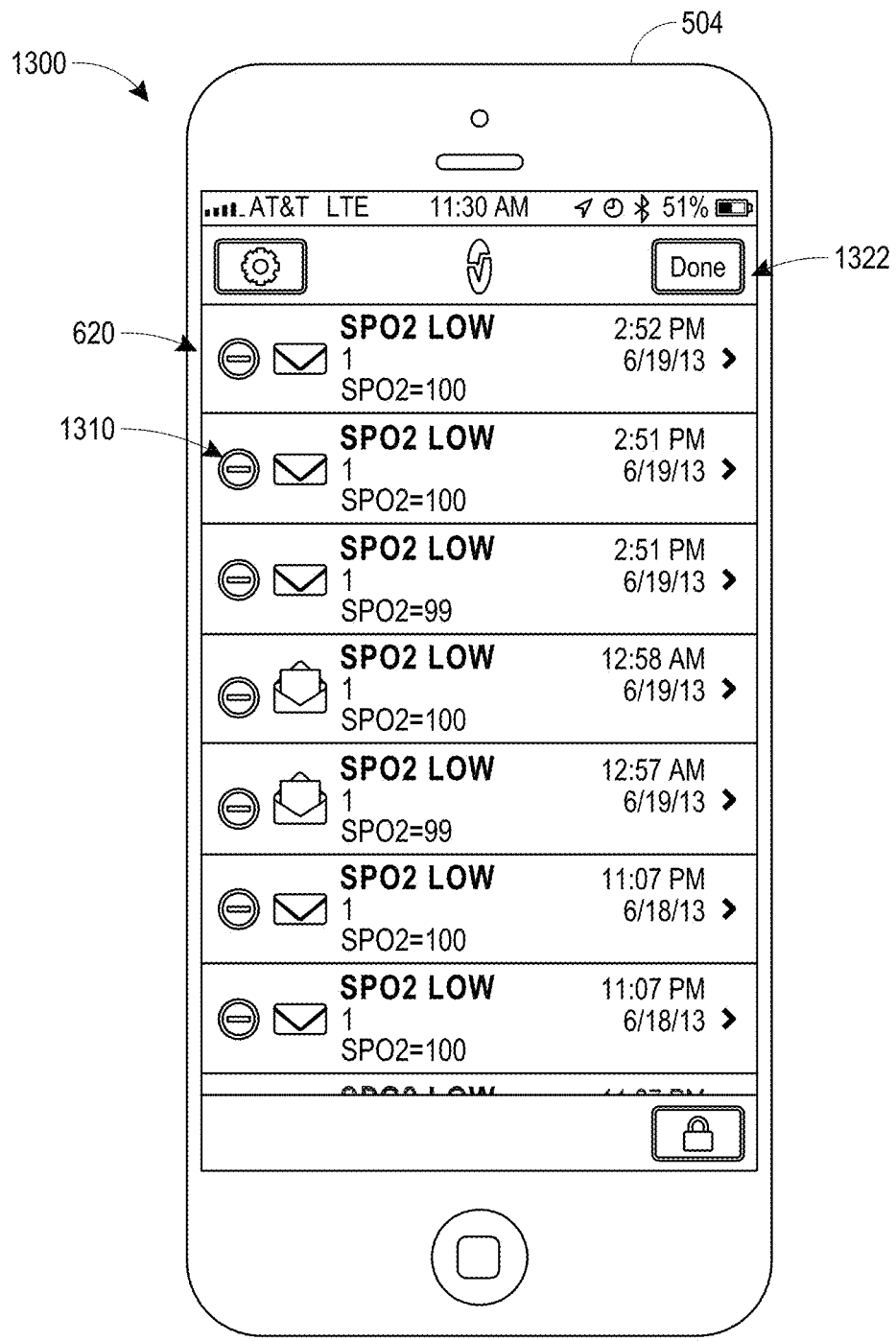

FIG. 13 depicts another user interface 1300 similar to the user interface 600 and 1200. The user interface 1300 may be accessed by selection of the edit button 622 in FIG. 6 or any of the previous screens that depicts the edit control 622. Selection of the edit control 622 can cause delete selector controls 1310 to be depicted next to the notifications 620.

Figure 14:
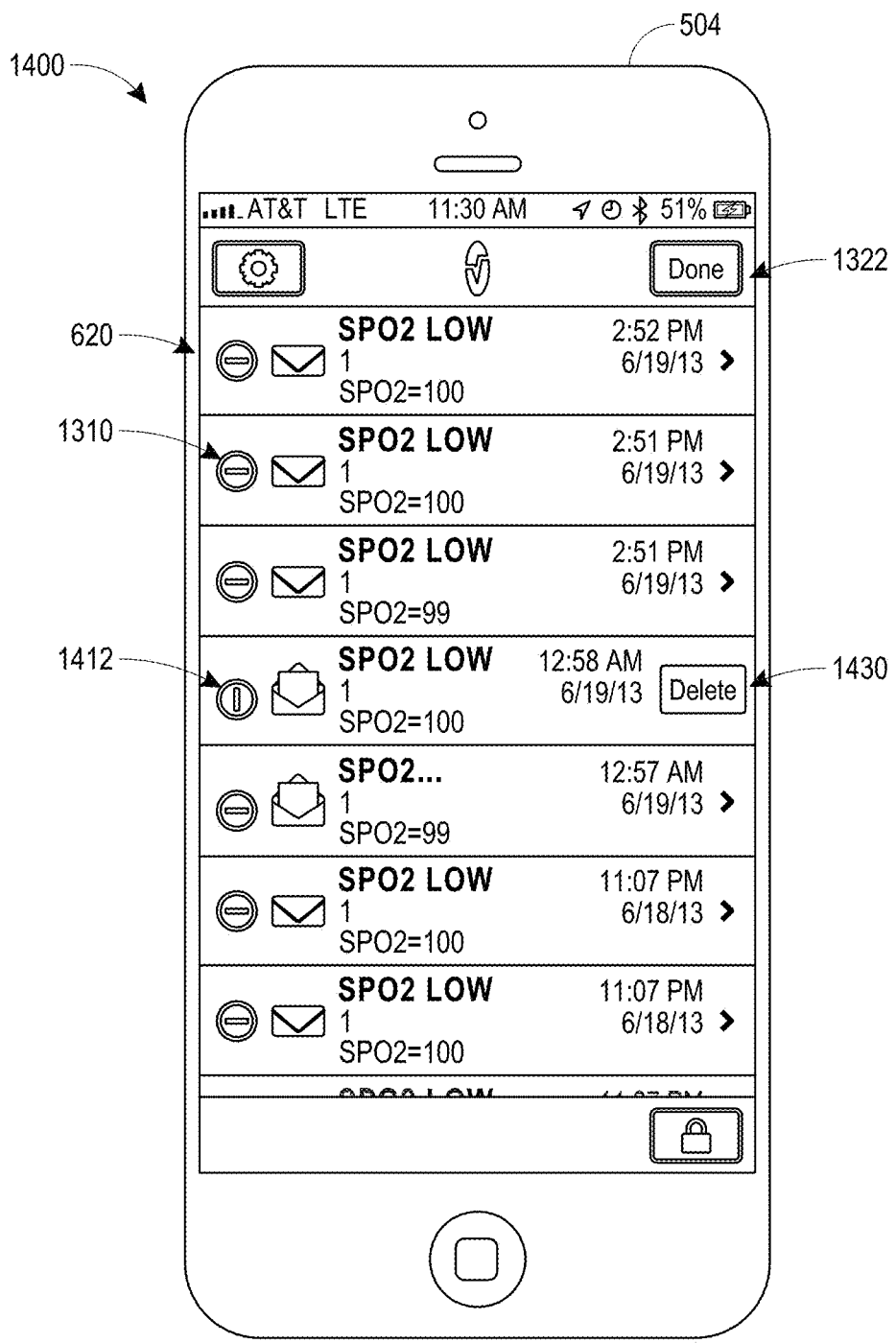

Selection of a deletion selector control 1310 can cause a user interface such as that shown in FIG. 14 to be displayed. The user interface 1400 includes a selected delete selector control 1412, which selection causes a delete button 1430 to be displayed in-line with the notification 620 selected for deletion. A user can select the delete button 1430 to cause the notification to be deleted and then select the done button 1322 to leave the edit view. Thus, in one embodiment, three user inputs are used (selecting the edit button, the delete selector control 1310, and then the delete button 1430) to delete a notification, thereby enabling deletions without having too few steps to make deletions too easy to accidentally perform. In other embodiments, however, there may be other mechanisms for deleting notification 620 such as long pressing to delete, swiping to delete, or the auto deletion scenario described above.

Figure 15:
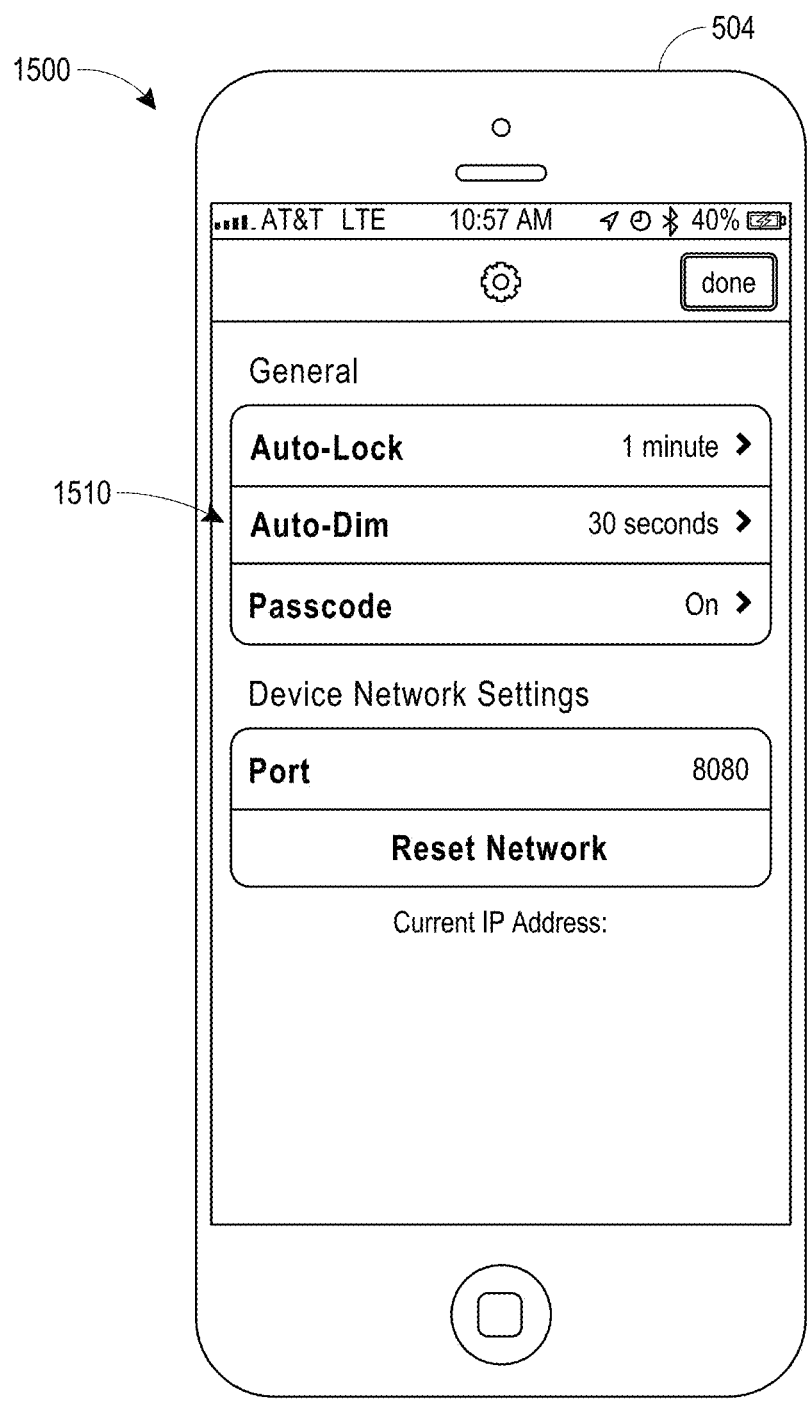

FIG. 15 depicts an example user interface 1500 that may be reached by selection of the settings control 620 from FIG. 6 and depicts various settings 1510 associated with an embodiment of the notification client 108. These settings 1510 include an auto-lock timer, an auto-dim timer, passcode function and network parameters such as a port for which to communicate with the MMS 310. Other settings may also be provided in other embodiments.

Figure 16:
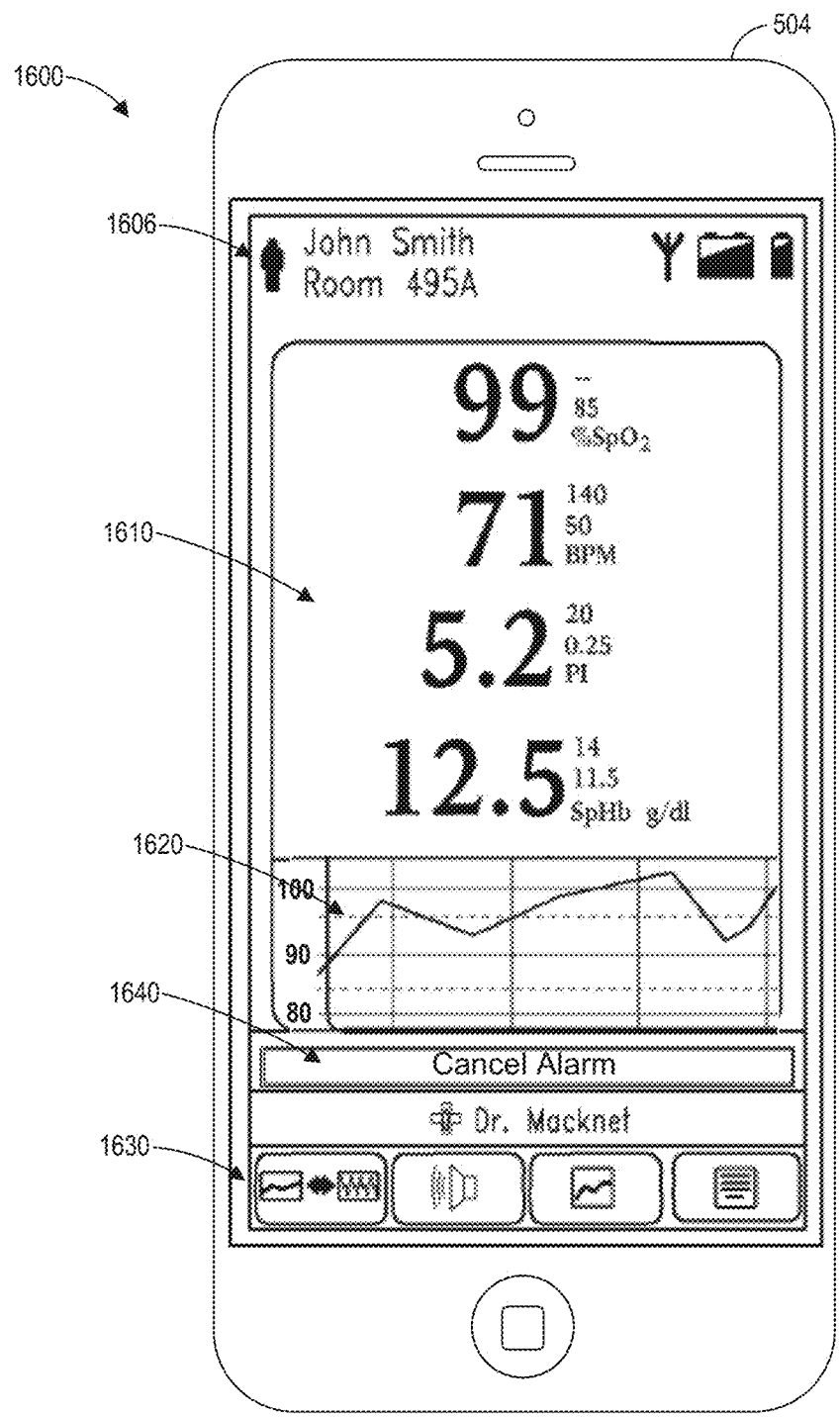

Turning to FIG. 16, another example user interface 1600 is shown that includes additional detailed patient information that may be accessed by selecting the additional details from any of the user interfaces described above or by other menu options not shown herein. The user interface 1600 includes patient biographical info 1606, parameter values 1610, and a parameter trend 1620 that depicts values of a selected parameter over time. The parameter trend 1620 can depict the parameter that triggered the alarm or another parameter and may be selected by the clinician. Although not shown, the wellness index described above or a trend thereof may also be shown.

One value of depicting the parameter trend 1620 and/or the parameter values 1610 in more detail can enable a clinician to determine whether the alarm is actionable. The parameter value 1610 and the trend 1620 can update as the clinician is observing the user interface 1600. Thus, the clinician can observe the parameter value 1610 and/or the trend 1620 to see if the patient comes out of the alarm state. As a result, the clinician may decide that the patient does not need intervention or perhaps that immediate intervention is not needed. The clinician can then use this information to prioritize other more serious alarms over this alarm.

In other embodiments, if the clinician determines that no intervention is necessary, the clinician can select a control 1640 to cancel the alarm remotely. In response to selection of the control 1640, the notification client 108 can send a message to the MMS 110, which sends an alarm cancellation message to the patient device 102.

The user interface 1600 also includes menu options 1630 to select between trend and parameter waveform views. In addition, the menu options 1630 can turn audio on or off. The audio may include audio obtained from a respiration sensor attached to the patient, which can detect the patient's breathing sounds. The audio may also include audio from a microphone attached to or coupled with the patient device 102, which can allow the clinician to communicate with the patient verbally. Video options are also available (see FIG. 17) for viewing a video of the patient. Video may include two-way video chat in an embodiment, such that the clinician device 504 captures video of the clinician and provides this video to the patient device (e.g., through the MMS or directly), which in turn outputs the video or outputs the video on a separate display, such as a television in the patient's room. The MMS can also route the video directly to a television or monitor in the patient's room. Through these audio and/or video features, the clinician can observe the health of the patient remotely, even while walking toward the patient's room to clear the alarm. The clinician can therefore anticipate in advance, based on what he or she sees and/or hears, what needs the patient may have, enabling the clinician to call for additional help, equipment, or medicines as necessary. Accordingly, providing audio and/or video of the patient to the clinician device can enable clinicians to improve patient outcomes.

In another embodiment, the user interface 1600 can be modified to depict the same user interface that is shown on the patient device, enabling the clinician to see exactly or substantially the same type of view as if he or she were to enter into the patient's room and view the patient device in person. In another embodiment, the user interface 1600 can depict a view of a second screen monitor that receives other parameters being monitored for the patient, such as a television that receives ventilation data or other data.

Any of these audio, video, and screen-sharing features can facilitate the performance of telemedicine or remote monitoring of patients.

Further, in some embodiments, the options 1630 enable the clinician to annotate an alarm to include a note as to what the clinician thinks should be done. The clinician device can transmit this annotated note to the patient device (e.g., through the MMS), which can display the note. Thus, a second clinician who sees a note written by a first clinician may have the benefit of the first clinician's thinking on the alarm, even if the first clinician cannot personally remediate the alarm. Similarly, the options 1630 can allow the clinician to dictate a recommended course of action, which can be sent to the patient monitor and played back.

Figure 17:
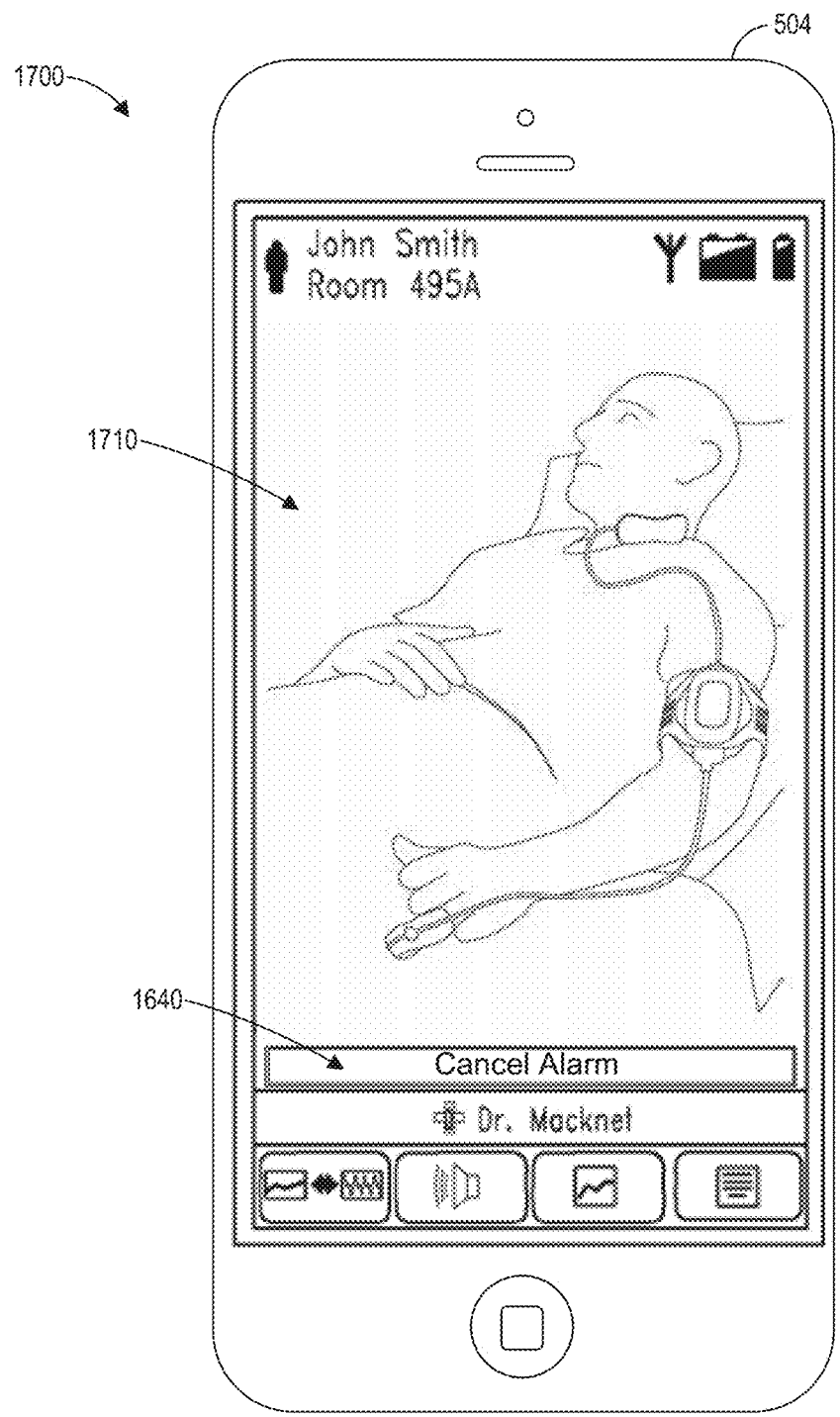

Turning to FIG. 17, another example user interface 1700 is shown, which depicts a video 1710 of the patient that may be obtained by a video camera installed on a patient device or other location in a patient's room. The video view can help the clinician determine the status of the patient and it may further facilitate the telemedicine features described above. If the clinician determines from the video 1710 that the patient is in suitable condition that would facilitate remediating the alarm, the clinician can select the cancel alarm button 614 as in FIG. 16 to remediate the alarm.

VI. Patient Admit Embodiments

Figure 18:
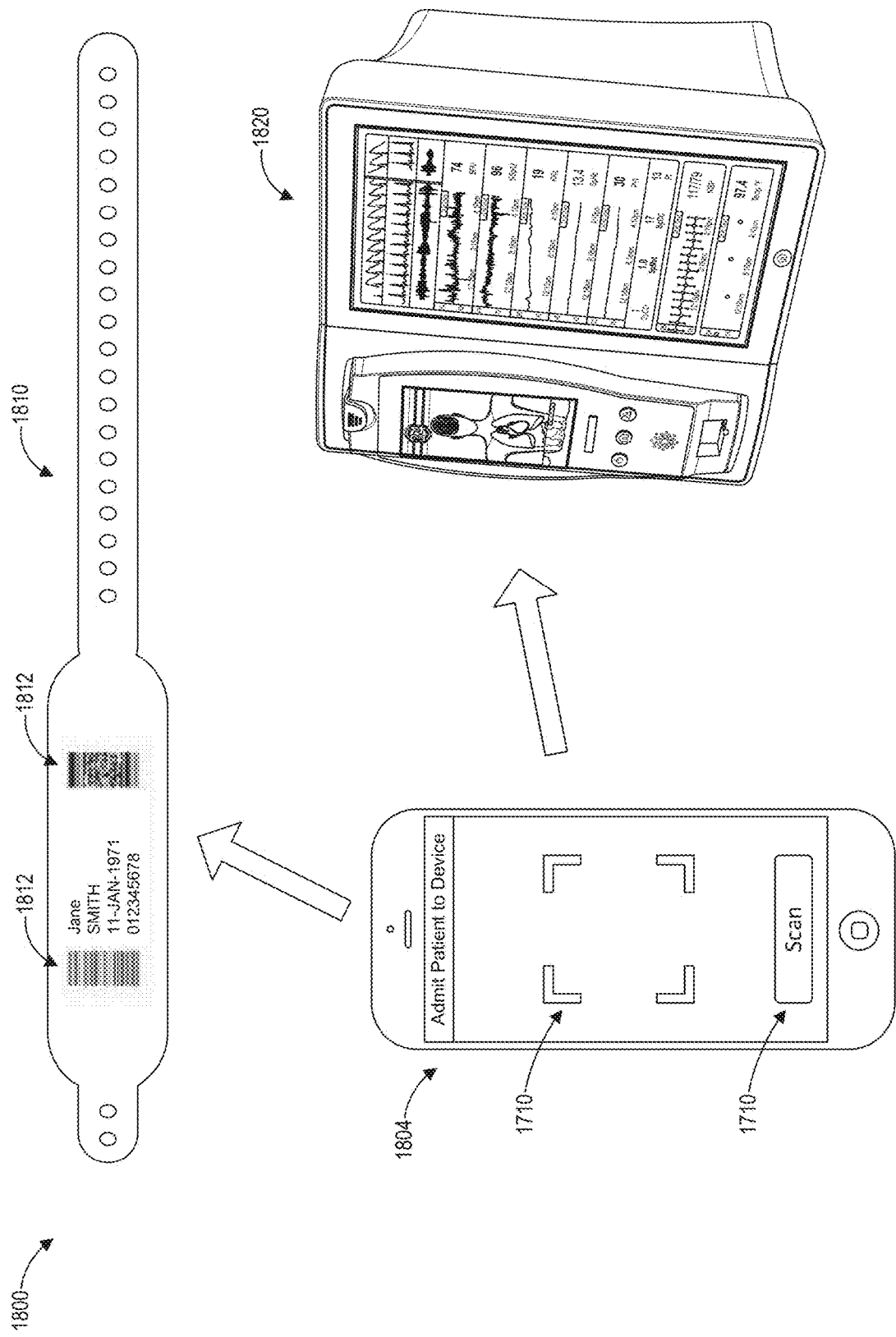
FIG. 18 depicts an example scenario for admitting a patient to a device or location.

Turning to FIG. 18, an example scenario 1800 is shown for admitting a patient to a device. In the scenario 1800, as described above with respect to the admit module 226 of FIG. 2, it can be desirable to automatically associate a patient with a device so as to reduce or eliminate errors that can occur through typing such information into a computer. Automatic patient-device association can also speed up the care of a patient by quickly facilitating the association of the patient with the device.

Admitting that patient to a device is distinct from admitting a patient to a hospital in one embodiment, although these two separate activities may in practice occur at the same time. In one embodiment, the patient is first admitted to the hospital, and during this process, information about the patient is stored in the MMS 110 or EMR 120. Subsequently, the patient may be assigned a room in the hospital and/or a patient device 102 (see FIG. 1) to monitor that patient. The patient may be admitted to the patient device so as to associate a profile of the patient in the MMS 110 with the patient device. Admitting the patient to the device can enable accurate tracking of the patient's movements through the hospital, accurate keeping of records in an electronic medical record (EMR) system associated with the MMS 110, accurate escalation of alarms with accurate patient data, as well as possibly other benefits.

In the depicted embodiment, a clinician device 1804 is shown that can include all the features of the clinician devices described herein. The clinician device 1804 can include the functionality of the admit module 112 or 226 described above with respect to FIGS. 1 and 2 and may, for instance, include the ability to scan machine readable codes, RFID tags, or the like. For instance, the clinician device 1804 includes a scanner view 1710 that enables a user to scan machine readable codes and a scan button 1710 that enables the user to select the scan button 1710 to cause the scan to occur by the clinician device 1804. In alternative embodiments, the clinician device 1804 does not include the scan button 1710 but instead automatically scans any image that it encounters and then determines whether the image includes a machine readable code. The scanner can automatically extract the information from the machine readable code accordingly.

A patient bracelet 1810 is also shown which includes barcodes 1812 that can be scanned by the clinician device 1804. Although two barcodes 1812 are shown in this example, one may be omitted in some embodiments. The two barcodes 1812 may be used for different purposes. A patient device 1820 is also shown that may also include a barcode that may be scanned by the clinician device 1804. In an embodiment, a clinician uses the clinician device 1804 to scan the patient bracelet 1810 and the patient device 1820 so as to associate the two together in physical computer storage. The clinician can scan the bracelet 1810 first or the device 1820 first. The clinician device 1804 can send data obtained from the scanned codes to the MMS so that the admit module 226 of the MMS can link together the device 1820 and the patient in computer storage. This linkage can enable the patient device 1820 to send data records associated with the patient to the EMR 120.

In other embodiments, instead of linking the patient bracelet 1810 with a patient device 1820, the clinician device 1804 can link the patient bracelet 1810 with a data record in the EMR 120 or MMS 110 that represents a location. Examples of such locations include a room, facility, bed, bassinette, or any other location in a clinical facility. As the patient is moved from room to room in a clinical facility, the clinician can use the clinician device 1804 to scan an identifier tag in or near or otherwise associated with (e.g., as a tag at the nurse's station) the new location (or new device in the new location). As a result, accurate records can be maintained for the patient and accurate alarm notifications may be sent, as described above.

In still other embodiments, the clinician device 1804 can use other technologies to automatically associate the patient bracelet 1810 with the patient device 1820 or patient location. For instance, the clinician device 1804 can scan an RFID tag in the patient bracelet 1810 and scan an RFID tag in the patient device 1820 or location associated with the patient so as to link the two together. Thus, more generally, the clinician device 1804 can scan identifier tags and cause the identifiers of those tags to be associated together.

Thus, the patient bracelet 1810 is an example of an identification tag that can be scanned optically (if including a machine-readable code such as a barcode) or wirelessly (e.g., if the bracelet 1810 includes an RFID tag). Similarly, a sticker or plate affixed to the patient device 1820 or location is also an example of an identification tag that can be scanned optically (if including a machine-readable code such as a barcode) or wirelessly (e.g., if the bracelet 1810 includes an RFID tag).

Figure 19:
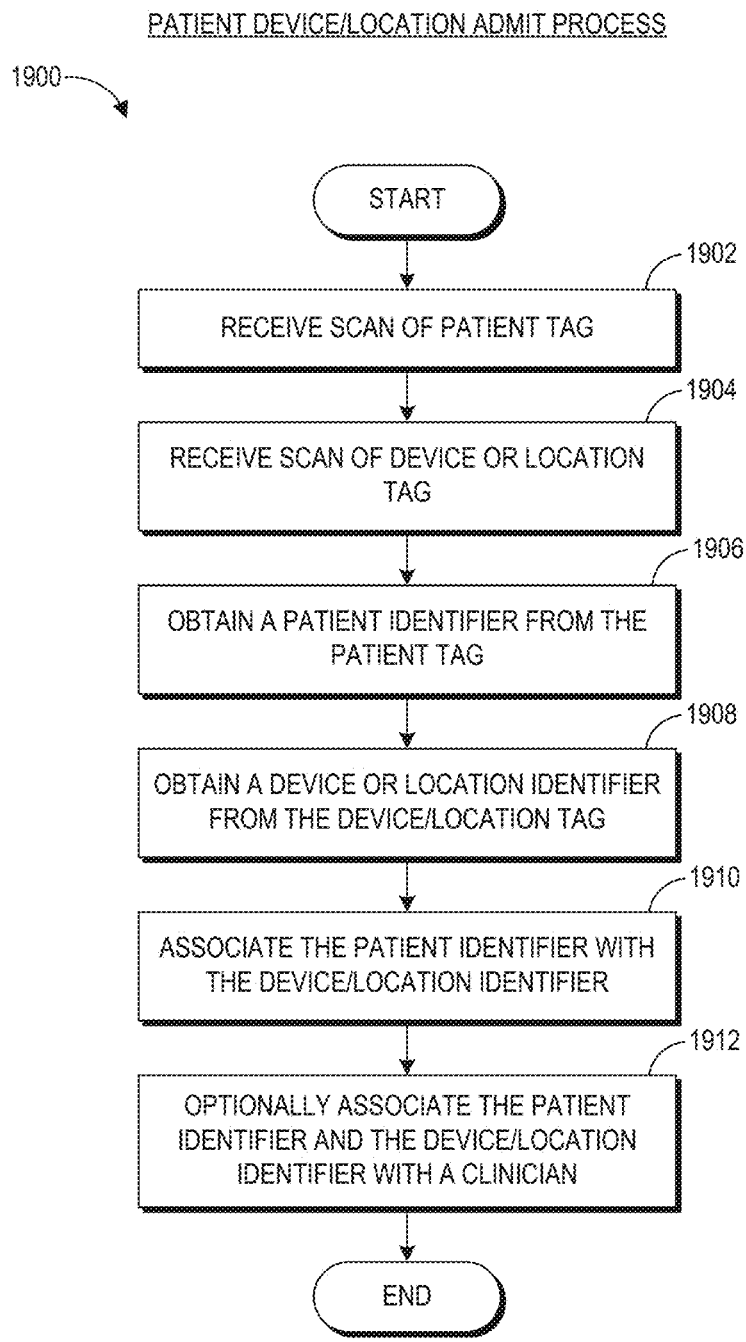
FIG. 19 depicts an example process for admitting a patient to a device or location.

FIG. 19 depicts an example process 1900 for associating a patient with a device or location. The process 1900 may be implemented by any of the systems or devices described herein. For convenience, the process 1900 will be described in the context of the clinician device, although other computing devices not described herein may implement the process 1900.

At block 1902, the clinician device receives a scan of a patient tag which may be an RFID tag, machine readable code or the like. At block 1904, the clinician device receives a scan of a device or location tag and obtains a patient identifier from the patient tag at block 1906. The clinician device obtains a device or location identifier from the device or location tag at block 1908.

The clinician device associates the patient identifier with the device or location identifier 1910 in an embodiment, for instance, by providing both of these identifiers to the admit module 226 described above with respect to FIG. 2. The admit module 226 can in turn store an association between the device or location and the patient in the EMR 120. At block 1912, the clinician device can optionally associate the patient identifier in the device or location identifier with a clinician, such as the clinician who is the user of the clinician device. As a result, in an embodiment, the MMS can know which clinician is assigned to the patient and which patient device is assigned to the patient programmatically.

Figure 20:
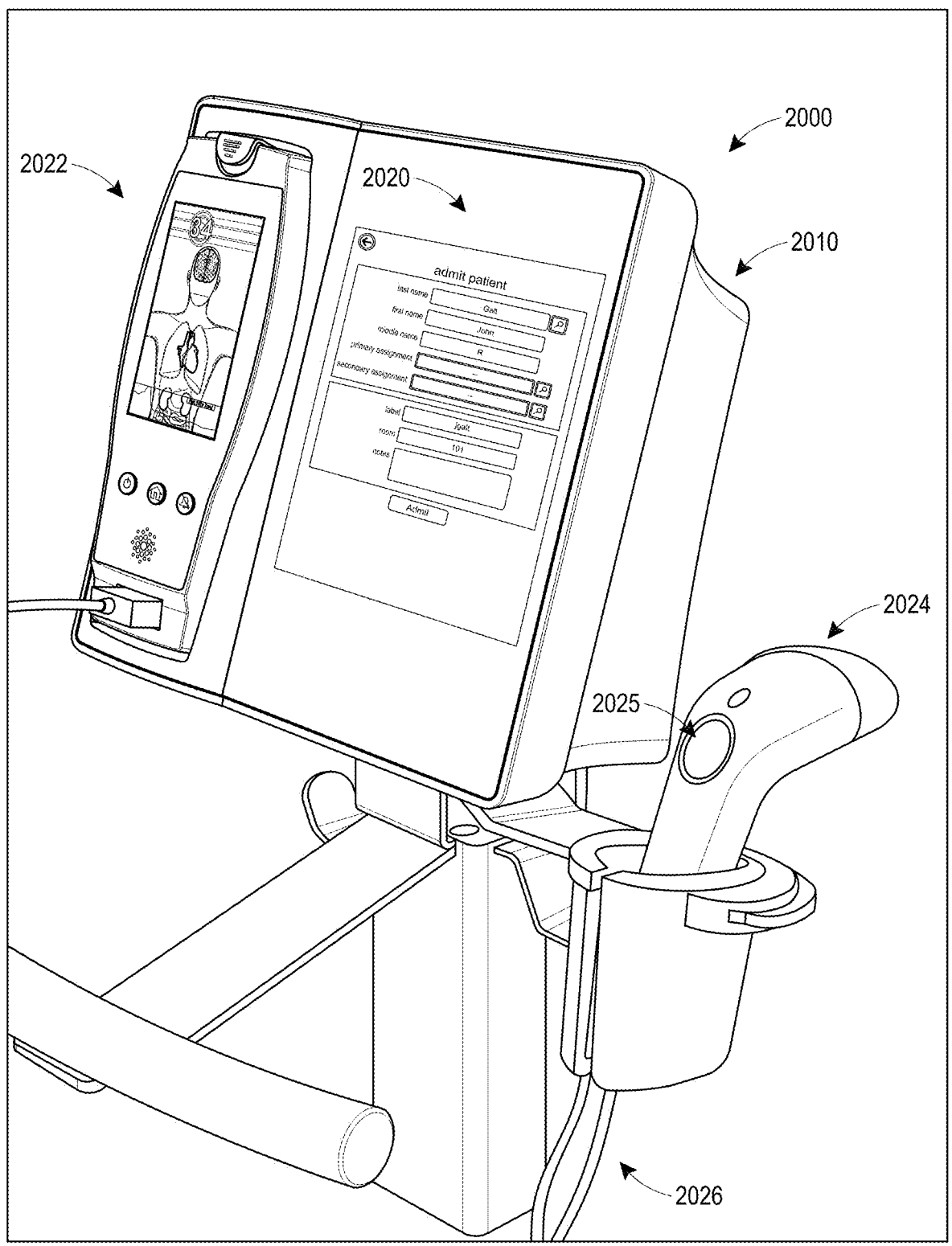
FIG. 20 depicts an embodiment of a patient monitoring device with a scanner for admitting the patient to the device.

FIG. 20 depicts an embodiment of a patient monitoring device 2000 with a scanner 2024 for admitting the patient to the device. The patient monitoring device 2000 is another example of the monitoring device 1820 and may include all the features thereof. Likewise, the patient monitoring device 2000 is an example of the patient devices 102 described above. The patient monitoring device 2000 includes a hub 2010 (which is an example of a patient monitor) and a portable physiological monitor (PPM) 2022. The PPM 2022 is also an example patient device 102 and connects to the hub 2010 via a docking port (obscured by the connection of the PPM 2022 to the hub 2010). The hub 2010 and PPM 2022 may have all the functionality of the corresponding hubs and PPMs described in U.S. application Ser. No. 13/651,167, titled "Medical Monitoring Hub," filed Oct. 12, 2012, the disclosure of which is hereby incorporated by reference in its entirety. For instance, physiological parameter data may be output on a display 2020 of the hub 2010 and/or on a display of the PPM 2022. In addition to their ordinary meaning, this specification often uses the terms "physiological monitor," "patient monitor," and "patient device" interchangeably.

In the embodiment shown, the display 2020 of the hub 2010 includes a patient admit screen that may implement some or all of the functionality described above with respect FIGS. 18 and 19. Additional examples of patient admit user interfaces are described in greater detail below with respect to FIGS. 21 through 25. The scanner 2024 shown is an example of an optical scanner that can be used instead of the clinician device 1804 to scan the identifier tags described above with respect to FIG. 18. The scanner 2024 can include electrical circuitry and/or a processor configured to cause an infrared beam to be emitted, such that when the user brings the scanner 2024 into close proximity with an identifier tag, the scanner 2024 reads a value associated with the identifier tag. A button 2025 on the scanner 2024 may be depressed by a user to cause a scan to occur. In another embodiment, the scanner 2024 is an RFID scanner, rather than an optical scanner, and may have suitable circuitry configured to scan an RFID identifier tag. A cable 2026 connects the scanner 2024 to the hub 2010 to convey scanned data to the hub 2010 (or the PPM 2010) so that the hub can perform the admit processing described above, including with respect to FIG. 19. The scanner 2024 may be wireless in other embodiments.

Figure 21:
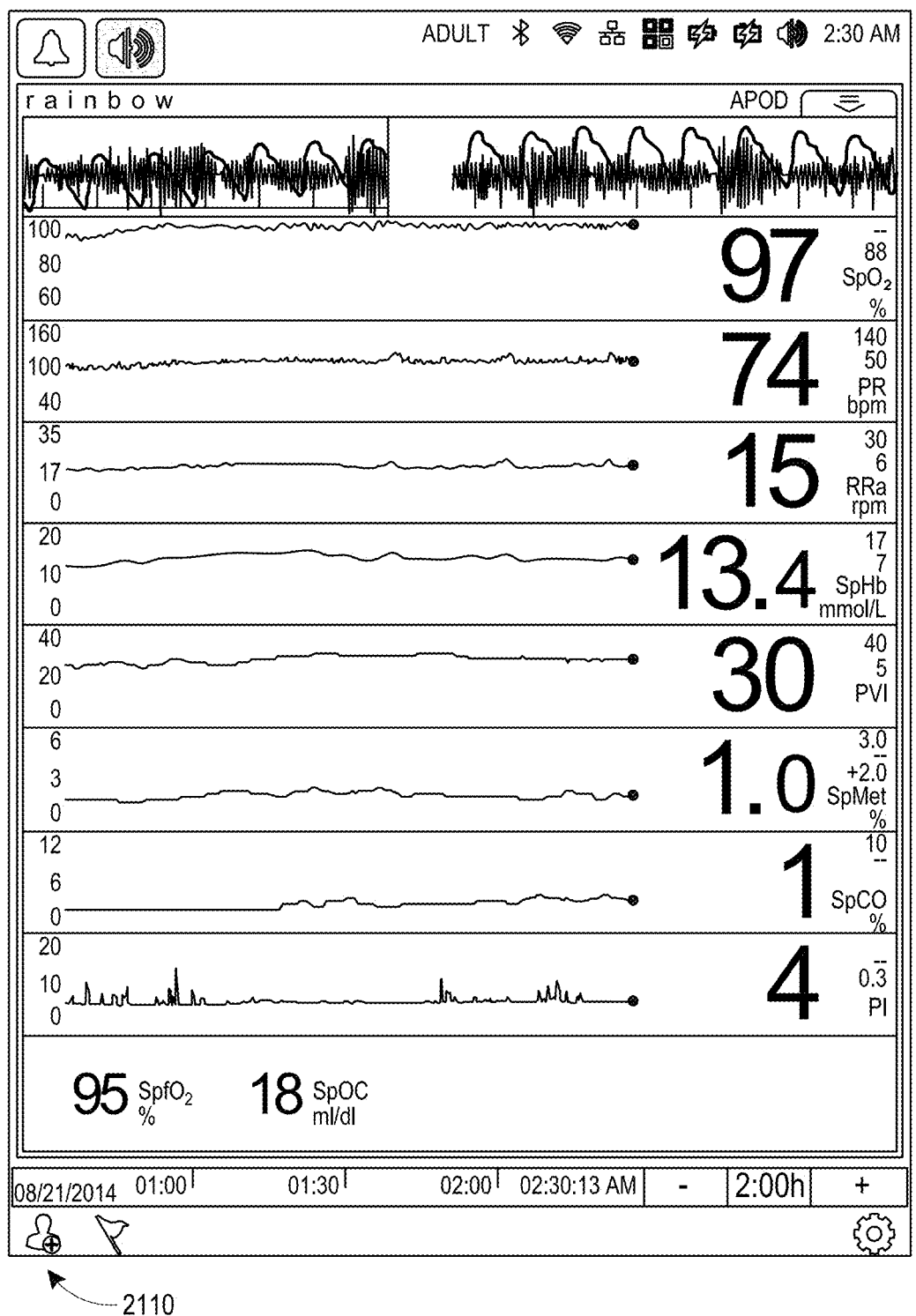
FIG. 21 depicts an example monitoring device user interface that includes functionality for initiating a patient admittance process.

FIG. 21 depicts an example monitoring device user interface that includes functionality for initiating a patient admittance process. The user interface can be implemented by any of the patient devices described herein, including patient devices 102, 1820, or 2000. The user interface shown in FIG. 21 displays numerous monitored physiological parameters of a patient. In addition, and admit icon 2110 is displayed. When pressed or otherwise selected (e.g., with a mouse) by a user (such as a clinician), the user can admit a patient to the patient device. Selecting the admit icon 2110 can enable a user to perform the scanning described above with respect to FIGS. 18 through 20. In another embodiment, selecting the admit icon 2110 can enable a user to perform a manual admit process without using the scanning technology described above.

FIGS. 22 through 25 depicts an example monitoring device user interface for admitting a patient to the device. These user interfaces can be implemented by any of the patient devices described herein, including patient devices 102, 1820, or 2000.

Referring specifically to FIG. 22, a user interface is shown that may be displayed by the patient device in response to the user selecting the admit icon 2110 of FIG. 21. The user interface shown includes a search button 2210 to enable a user to search for a patient's record (or the name of the patient) in the MMS 110 or EMR 120 (see FIG. 1). When the patient is admitted to the hospital, or at an earlier time, a patient record may be created in the MMS 110 or EMR 110, which may subsequently be searched for at the patient device to associate that patient with the device. As an alternative (or additional feature) to searching, a user may type the text of the patient's last name into a text box of the user interface next to the search button 2210.

Fields 2220 are also included for manually inputting a patient's first name and middle name. Search boxes 2230 are also provided for entering a primary assignment and an optional secondary assignment. The primary assignment may refer to a clinician assigned to be the primary caregiver of the patient, while the secondary assignment can refer to a clinician assigned to be a secondary caregiver of the patient. The primary and secondary assignments can be used in part to manage patient escalation using any of the escalation features described above. For instance, an alarm generated by the patient device may initially be sent to a clinician device of the primary assignment and may subsequently be escalated to a clinician device of the secondary assignment.

Text boxes 2240 are also provided for inputting a label or short name for the patient, a room number associated with the room that the patient is staying in at the hospital or clinical facility, and any notes a clinician wishes to provide.

Figure 23:
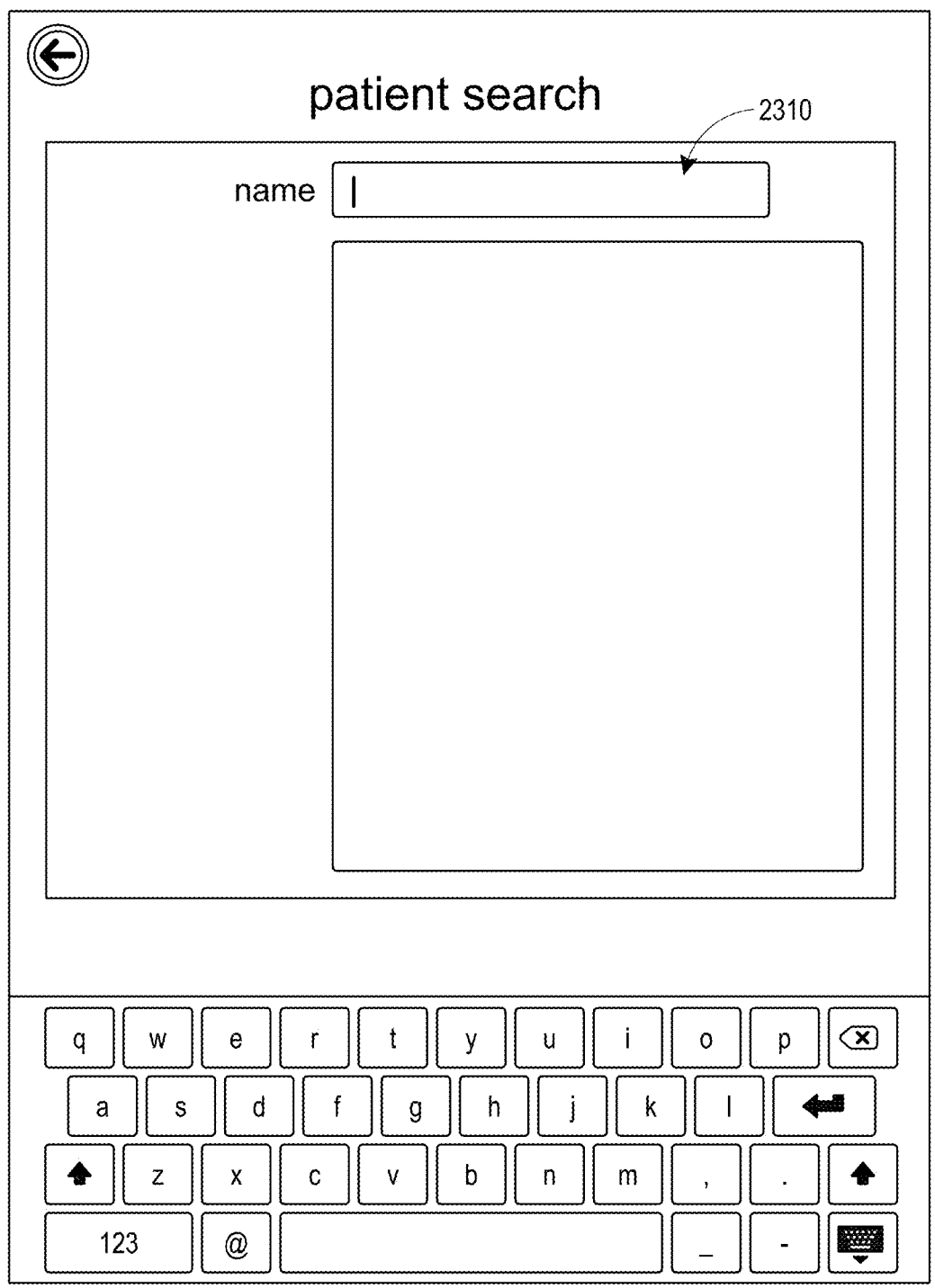
Figure 24:
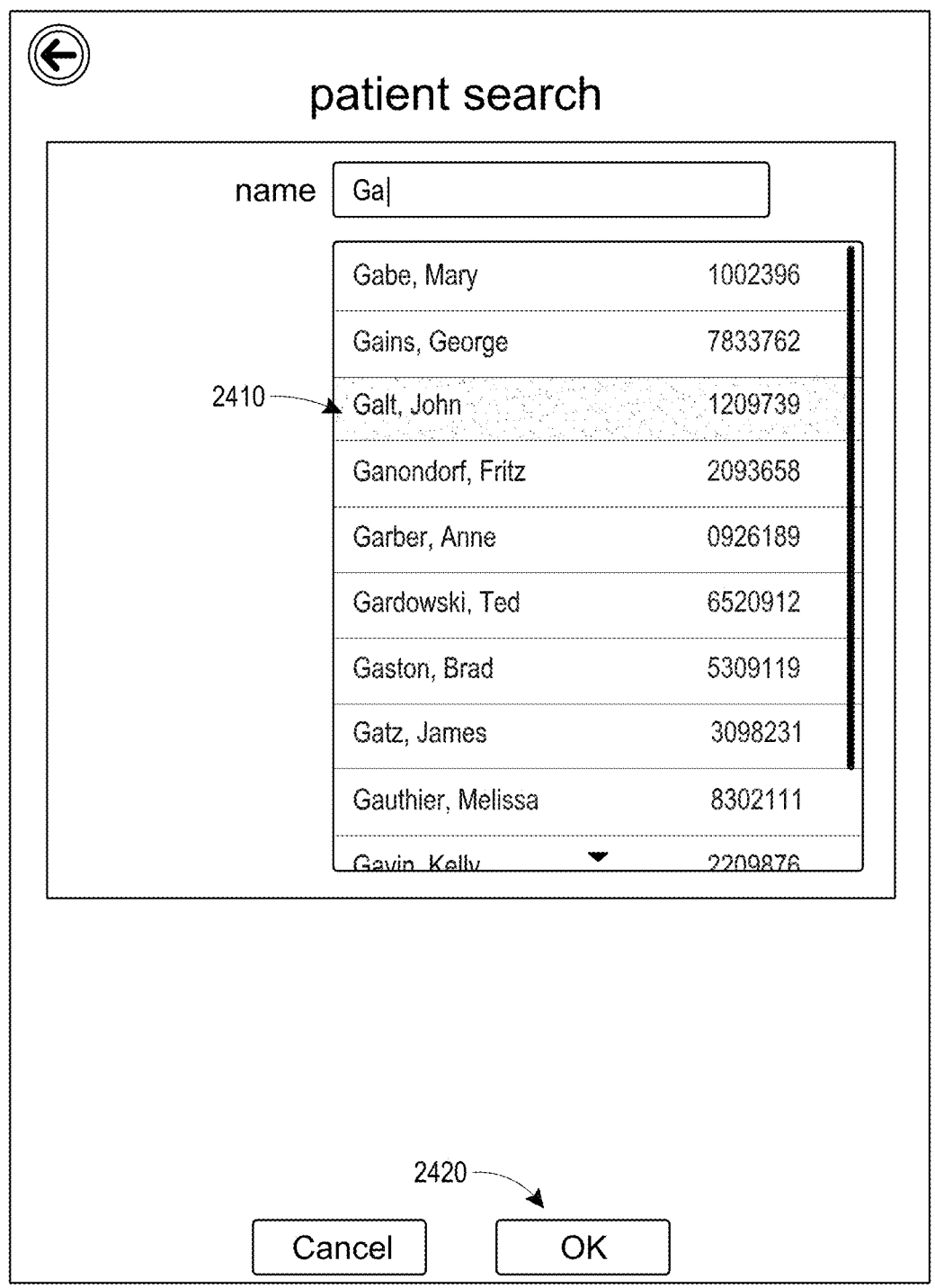

FIG. 23 depicts another example user interface with the text box 2310 for searching for patient. This user interface may be reached in an embodiment after a user selects the search button 2210 of FIG. 22. FIG. 24 shows another example user interface with example search results 2410 shown, which may be reached after the search is conducted in FIG. 23. The user can select a patient's name and touch an Okay button 2422 to continue the admit process.

FIG. 25 depicts a similar screen to FIG. 22, this time with patient name, label, and room number filled in. Any of this data may be populated automatically or manually as described above, based on the results of the search or based on user data entry. An admit button 2510 may be selected by the user to admit the user to the device. Upon selection of the admit button 2510 by a user, the patient device can send a notification or message to the MMS 110, which can store an identifier of the device together with the record of the patient in data storage, such as the EMR 120.

VII. Vital Signs Verification and Submission Embodiments

Periodically, nurses in a clinical facility read a patient's vitals and write those vitals down in a patient's chart, walk to the nurse's station, and input those vitals into computer to be associated with an electronic medical record of the patient. Examples of vitals that may be monitored by the nurse and written down include temperature, pulse, respiration, blood pressure, oxygen saturation, pain assessment, and level of consciousness (see also FIG. 27). Intervals for entering patient vitals may vary based on different monitoring situations and in different clinical facilities. One example interval would be to enter a patient's vitals half an hour after the patient has been admitted, and once every hour for four hours, and then once every 6 to 8 hours once the patient has stabilized.

Writing down vitals on a chart and physically entering the vitals into the computer can be time intensive and inaccurate. The patient devices described above can automatically send many vital signs to the electronic medical record of the patient associated with the MMS 110, but other vital signs are not continuously monitored by the patient devices. Thus, clinicians typically still enter such vital signs manually on paper in the process outlined above. An alternative approach is described below with respect to FIGS. 26 through 28.

Figure 26:
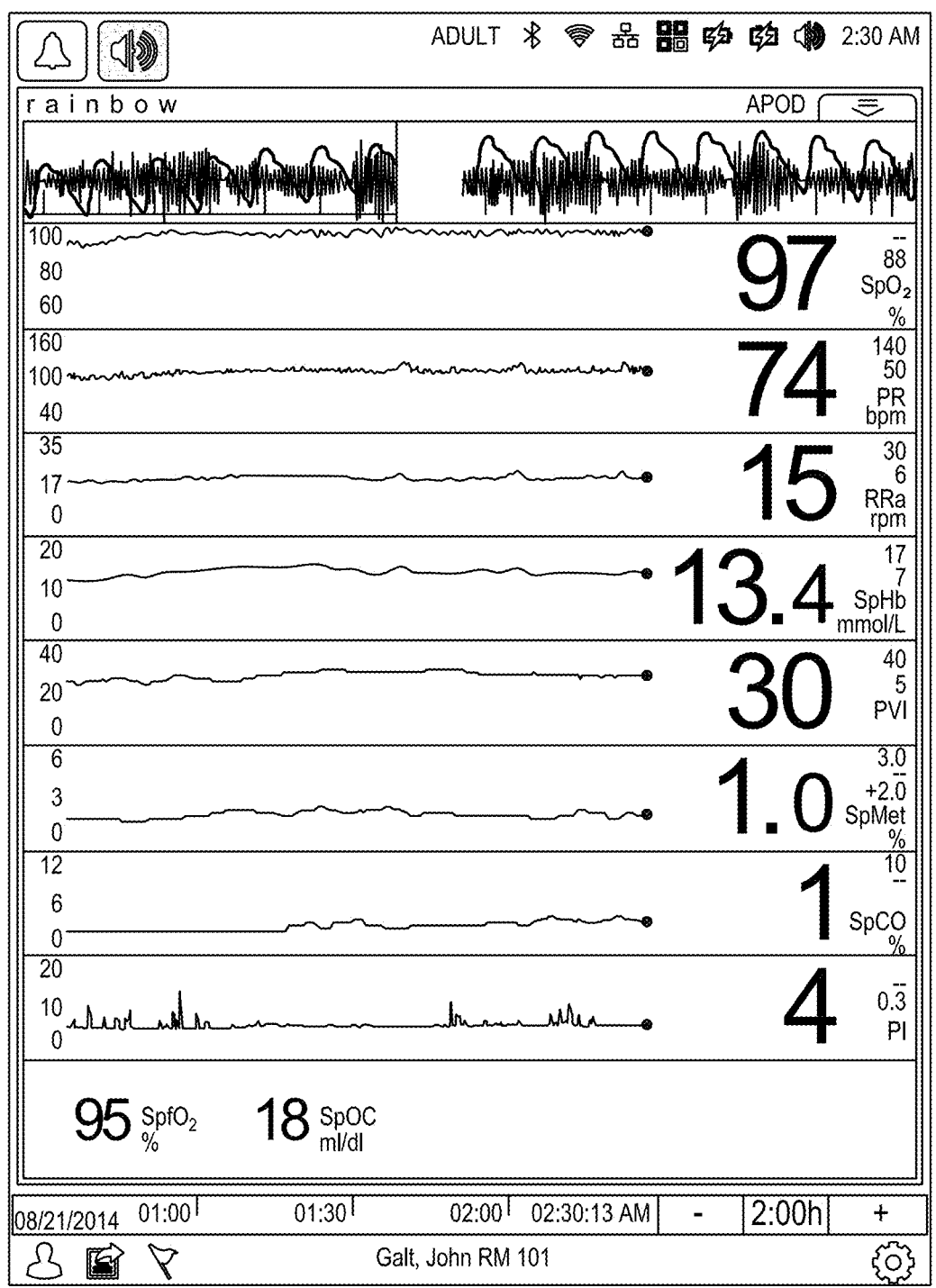
FIG. 26 depicts an example monitoring device user interface that includes functionality for initiating a vital signs submission process for an admitted patient.
Figure 28:
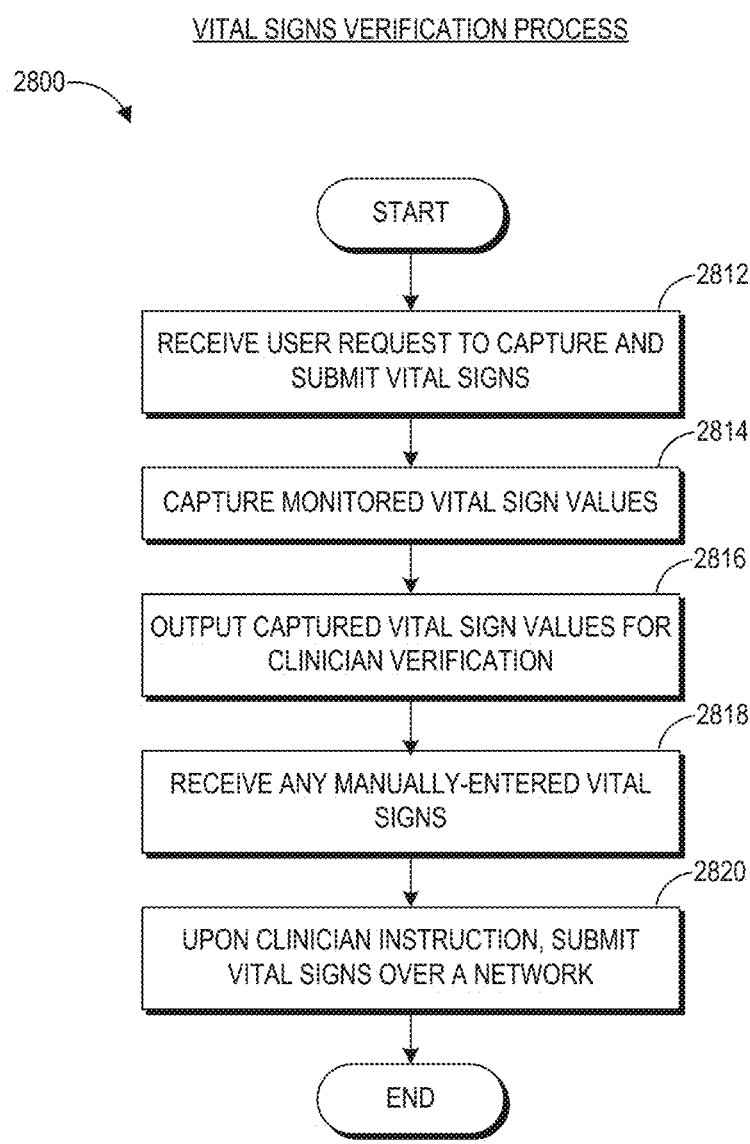
FIG. 28 depicts an embodiment of a process for verifying vital signs.

The approaches described with respect to FIGS. 26 to 28 may be implemented with an admitted patient or non-admitted patient, although doing so with an admitted patient may provide the advantage of simplifying the process of associating the vital signs with the correct patient record. Alternatively, vital signs may be submitted and later associated with a patient record (e.g., at the nurse's station or after the patient is admitted to the device). Both the automatic scanning or manually-inputted admit processes may be used prior to or after the vital signs verification and submission embodiments described below. The following embodiments can be implemented at least in part by the vital signs verification component 114 (see FIG. 1).

FIG. 26 depicts an example monitoring device user interface that includes functionality for initiating a vital signs submission process for an admitted patient. Once a patient has been admitted, vital signs can be captured by the patient device and/or by the clinician and submitted via the patient device to the MMS 110 for inclusion in the patient's electronic medical record. An icon 2610 in the user interface can be selected by a user to initiate a vitals verification and submission process.

Selection of the icon 2610 can cause a user interface such as the one shown in FIG. 27 to be displayed on the patient device. In particular, FIG. 27 depicts an example monitoring device user interface that includes functionality for submitting vital signs. Some vital signs 2710 are automatically captured by the patient device at the point in time that the user selects the icon 2610. Fields 2720 are provided for a user to optionally input additional vital signs not continuously monitored, including temperature, blood pressure (or noninvasive blood pressure (NIBP)), level of consciousness, and a pain scale rating. Each of the fields 2720 may be drop-down boxes or text boxes that the user can enter text or scroll down to select a value. Other fields for other spot-check sensor values or other patient parameter data, not shown, may also be displayed in other embodiments.

The level of consciousness values may include qualitative measures of consciousness, such as on a scale including alert, drowsy, lethargic, obtunded, and coma. Other scales may also be used. The pain scale may be a 1 to 10 pain scale rating, where 10 is the most severe pain and 1 is the least severe or zero pain. Other scales may also be used. A nurse can observe the level of consciousness campaign level and input the same in the fields 2720 with or without input from the patient.

An approved button 2730 is provided and may be selected by the user to submit the vital signs to the MMS 110 for inclusion in the EMR 120.

FIG. 28 depicts an embodiment of a process 2800 for verifying vital signs. The process 2800 may be implemented by any of the patient devices described above, including the patient device 102, 1820, or 2000. The process 2800 can cause the user interfaces described above with respect to FIGS. 26 and 27 to be output for display. Corresponding user input can be received in those user interfaces and can be sent to the MMS 110 as described above.

At block 2812, the patient device receives a user request to capture and submit vital signs. For instance, the user may select the icon 2610 in the user interface of FIG. 26 to initiate the vital signs verification and submission process. At block 2814, the patient device automatically captures monitored vital sign values at that point in time (e.g., from a most recent or recent value stored in a memory device of the patient monitor). The patient device outputs the captured vital sign values for clinician verification at block 2816. An example display including such values is described above with respect to FIG. 27.

At block 2818, the patient device receives any manually entered vital signs. Such manually entered vital signs may be implemented using the user interface of FIG. 27 or the like. Upon clinician instruction (such as by selection of the Okay button 2730 of FIG. 27), the patient device submits the vital signs over a network (e.g., to the MMS 110) at block 2820.

VIII. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

Each of the user interfaces shown includes one or more user interface controls that can be selected by a user, for example, using a browser or other application software associated with a patient or clinician device. The user interface controls shown are merely illustrative examples and can be varied in other embodiments. For instance, buttons, icons, dropdown boxes, select boxes, text boxes, check boxes, slider controls, and other user interface controls shown may be substituted with other types of user interface controls that provide the same or similar functionality. Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input, or keyboard input, among other user interface input options.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor.

The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A system for managing alarm notifications, the system comprising:
an alarm notification component comprising physical computer hardware configured to:
receive, from multi-patient monitoring computing device, an alarm notification regarding an alarm at a patient device;
in response to receiving the alarm notification, transmit, to the multi-patient monitoring computing device, a first indication that the alarm notification was received by the clinician device, wherein the first indication provides information to the multi-patient monitoring computing device to not accelerate escalation of the alarm;
electronically generate a user interface configured to output an indication of the alarm notification to a clinician user and a user interface control selectable by the clinician user to respond to the alarm notification;
determine that the indication of the alarm notification was viewed by the clinician user at the clinician device but that the clinician user has not yet responded to the indication of the alarm notification;
in response to determining that the indication of the alarm notification was viewed by the clinician user but that the clinician user has not yet responded to the indication of the alarm notification, transmit, to the multi-patient monitoring computing device, a second indication that the alarm notification was viewed by the clinician user but that the clinician user has not yet responded to the indication of the alarm notification, wherein the second indication provides information to the multi-patient monitoring computing device to not accelerate escalation of the alarm;
receive an input from the clinician user, via the user interface, indicating that the clinician user has declined handling the alarm; and
in response to receiving the input, transmit, to the multi-patient monitoring computing device, a response to the alarm notification indicating that the clinician user has declined handling the alarm and so as to enable escalation of the alarm by the multi-patient monitoring computing device.

2. The system of claim 1, wherein the alarm notification component is implemented in a mobile device.

3. The system of claim 2, wherein the mobile device is restricted to a kiosk mode.

4. The system of claim 1, wherein the response indicates that the clinician user has marked the alarm notification as unread.

5. The system of claim 1, wherein the response indicates that the clinician user has marked the alarm notification as no longer actionable.

6. The system of claim 1, wherein the alarm notification component is further configured to access trend data associated with a physiological parameter that is a subject of the alarm and output the trend data for presentation to the clinician user.

7. The system of claim 1, wherein the alarm notification component is further configured to access video associated with the patient and output the video for presentation to the clinician user.

8. The system of claim 1, wherein the alarm notification component is further configured to receive an escalation or re-escalation of the alarm notification.

9. The system of claim 1, wherein the alarm notification component is further configured to output an indication of whether the alarm has been cleared.

10. The system of claim 1, further comprising an admit component configured to provide functionality configured to:
- receive a first scan of a first tag associated with the patient;
- receive a second scan of a second tag associated with the patient device or a patient location; and
- associate a first identifier of the first tag with a second identifier of the second tag.

11. The system of claim 10, wherein one or both of the first and second tags comprise machine-readable codes or radio-frequency identifier (RFID) tags.

12. The system of claim 10, wherein the admit component is further configured to transmit the first and second identifiers to an electronic medical records (EMR) system.

13. The system of claim 10, wherein the location comprises one or more of the following: a room, a bed, and a bassinet.

* * * * *